(12) United States Patent
Gao

(10) Patent No.: US 11,097,032 B2
(45) Date of Patent: Aug. 24, 2021

(54) SCENT DIFFUSION DEVICE

(71) Applicant: Guangzhou Zhihuagu Intellectual Property Service Co., Ltd., Guangzhou (CN)

(72) Inventor: Xiaoyang Gao, Xuchang (CN)

(73) Assignee: GUANGZHOU ZHIHUAGU INTELLECTUAL PROPERTY SERVICE CO., LTD., Guangzhou (CN)

( * ) Notice: Subject to any disclaimer, the term of this patent is extended or adjusted under 35 U.S.C. 154(b) by 36 days.

(21) Appl. No.: 16/672,461

(22) Filed: Nov. 3, 2019

(65) Prior Publication Data
US 2020/0188549 A1 Jun. 18, 2020

Related U.S. Application Data

(63) Continuation of application No. PCT/CN2019/096661, filed on Jul. 19, 2019.

(30) Foreign Application Priority Data

Dec. 12, 2018 (CN) .......................... 201822085191.2

(51) Int. Cl.
*A61L 9/14* (2006.01)
(52) U.S. Cl.
CPC ........... *A61L 9/14* (2013.01); *A61L 2209/133* (2013.01); *A61L 2209/134* (2013.01)
(58) Field of Classification Search
None
See application file for complete search history.

(56) References Cited

FOREIGN PATENT DOCUMENTS

| CN | 201832737 U | * | 5/2011 |
| CN | 105879099 A | * | 8/2016 |

OTHER PUBLICATIONS

Gao, X. CN201832737U—translated document (Year: 2011).*
Global Industrial-Global Industrial™ Automatic Air Freshener Dispenser. Global Industrial.com [online] [retr. Mar. 16, 2021], pp. 1-2. https://www.globalindustrial.com/p/janitorial-maintenance/bathroom/odor-control/global-153-automatic-air-freshener-dispenser-white?infoParam.campaignId=T9F&gclid=EAlalQobChMlubKlwrG17wlVyJ-zCh3OHAsREAYYBCABEgLeDvD_BwE (Year: 2015).*
Gao, X (CN105879099A)—translated document (Year: 2016).*

* cited by examiner

*Primary Examiner* — Jelitza M Perez
(74) *Attorney, Agent, or Firm* — Hemisphere Law, PLLC; Zhigang Ma

(57) ABSTRACT

The present disclosure discloses a scent diffusion device including an air pump, an atomizer and a liquid storage bottle. Wherein the atomizer is connected to the air pump and the liquid storage bottle, an atomizing chamber is disposed in the atomizer, a gas passage and a liquid passage is disposed in the atomizer. The gas passage is connected to the air pump and is contracted to form a gas outlet. The liquid passage is connected to the inside of the liquid storage bottle and is contracted to form a liquid outlet. The gas outlet is located at the liquid outlet and blows from the side of the liquid outlet to the other side of the liquid outlet. The atomizing chamber is connected to the gas outlet and the liquid outlet, and the atomizer is further provided with a mist outlet.

11 Claims, 25 Drawing Sheets

SCENT DIFFUSION DEVICE

RELATED APPLICATIONS

The present application is a National Phase of International Application Number PCT/CN2019/096661, filed on Jul. 19, 2019, and claims the priority of China Application No. 201822085191.2, filed on Dec. 12, 2018.

FIELD OF THE DISCLOSURE

The present disclosure relates to an incense equipment field, in particular to a scent diffusion device.

BACKGROUND OF THE DISCLOSURE

With the continuous improvement of living standards, more and more people pay more attention to the quality of life. People not only need beautiful and clean living and working places, but also need clean and odorless air. In order to improve the air environment, people often use perfume or essential oil in the room to improve the air quality in the space, so as to keep the air in the room fresh, eliminate odor and disinfect. However, spraying perfume or essential oil in a room is troublesome, and it is necessary to spray frequently to maintain the fragrance, and since the sprayed perfume particles are large, the range of drifting is small. Therefore, this method is inefficient and wasteful.

Based on this, people have invented a scent diffusion device, which is used to atomize perfume or essential oil, so that the fragrance diffuses into the air to improve the quality of the air. The prior art diffuser utilizes the siphon principle to draw liquid essence from the essential oil bottle and atomizes the fragrance through the atomizing core to diffuse into the air. The atomizer is relatively easy to use, but it also has the following problems: 1. In order to save the essential oil and make the discharged fine oil particles more delicate, the atomizing core needs to adopt a very fine liquid passage, and the processing difficulty is relatively large; 2. Since the essential oil generally has a certain viscosity, and the liquid passage of the atomizing core is too thin, it is easy to cause the problem that the liquid outlet channel is blocked.

SUMMARY OF THE DISCLOSURE

Based on this, it is necessary to provide a scent diffusion device that is finely sprayed and not easily clogged.

The present disclosure provides a scent diffusion device, including an air pump, an atomizer and a liquid storage bottle, wherein the atomizer is connected to the air pump and the liquid storage bottle, an atomizing chamber is disposed in the atomizer, a gas passage and a liquid passage is disposed in the atomizer, one end of the gas passage is connected to the air pump through a vent line, and the other end is contracted to form a gas outlet, one end of the liquid passage is connected to the inside of the liquid storage bottle through a pipe, and the other end is contracted to form a liquid outlet, the atomizing chamber is connected to the gas outlet and the liquid outlet, and the atomizer is further provided with a mist outlet connected to the atomizing chamber.

Preferably, the ratio of the maximum inner diameter of one end of the gas passage connected to the vent line to the inner diameter of the gas outlet is greater than 3, preferably between 5 and 20, and/or the ratio of the maximum inner diameter of one end of the liquid passage connected to the pipe to the inner diameter of the liquid outlet is greater than 3, preferably between 5 and 20.

Preferably, the bottom wall of at least a portion of the vent line is higher than the gas outlet; and/or the mist outlet is inclined from the inside to an outside with respect to the liquid storage bottle.

Preferably, the scent diffusion device further includes a power plug and a housing, the liquid storage bottle, the atomizer and the air pump are located inside the housing, the mist outlet is exposed from the housing, the plug end of the power plug protrudes to the outside of the housing, the other end of the power plug is fixedly connected to the housing, and the power plug is electrically connected to the air pump.

Preferably, the mist outlet is disposed on the other side of the housing opposite the power plug.

Further, the housing includes an upper housing and a lower housing, the upper housing and the lower housing are detachably connected, the air pump and the atomizer are disposed in the upper housing, the power plug is fixed to the upper housing, and the upper housing is provided with a connecting portion, the liquid storage bottle is screwed with the connecting portion, the lower housing is provided with a receiving chamber, and the liquid storage bottle is housed in the receiving chamber.

Preferably, the scent diffusion device further includes an outer housing and an inner housing, the inner housing being mounted in the outer housing and detachably connected to the inner wall of the outer housing, an air pump installation chamber is formed on the inner housing, the air pump is installed in the air pump installation chamber, the inner housing is further provided with an air pump connection joint, and the air pump connection joint is connected to the air pump through a gas pipe; the atomizer and the liquid storage bottle are installed in the outer housing and outside the inner housing, the atomizer is provided with an atomizing connection joint, the atomizing connection joint is connected to the gas passage, and the atomizing connection joint is plugging sealed with the air pump connection joint.

Preferably, a plurality of buckles is disposed on the inner wall of the outer housing, the inner housing is provided with a a plurality of holders engaged with the buckles respectively, and the inner housing is detachably coupled to the inner wall of the outer housing by the buckles and the holders.

Preferably, a limiting member is further fixed on the inner wall of the outer housing, the limiting member is an elastic member, and the limiting member abuts on an outer wall of the inner housing.

Preferably, the scent diffusion device further includes an outer housing and an inner housing, the inner housing being mounted in the outer housing, wherein the inner housing is formed with an air pump installation chamber, the air pump is installed in the air pump installation chamber, an air pump connection joint is further disposed on the inner housing, the air pump connection joint is connected to the air pump through a gas pipe, the atomizer and the liquid storage bottle are installed in the outer housing and outside the inner housing, and the atomizer is provided with an atomizing connection joint, the atomizing connection joint is connected to the gas passage, the air pump connection joint is made of a silicone material, and the atomizing connection joint is inserted into the air pump connection joint to be in sealing engagement with the air pump connection joint.

Preferably, the atomizer includes an atomizing base and an atomizing core, the atomizing base is connected to the air pump, the atomizing core is mounted on the atomizing base, and the gas outlet and the liquid outlet are both disposed on the atomizing core.

Preferably, the atomizing core is detachably connected to the atomizing base, and the atomizing core is integrally formed of a plastic material.

Preferably, the atomizing base is provided with a convex air guiding tube and a convex liquid suction tube, the air guiding tube and the liquid suction tube are arranged in parallel and spaced apart, the atomizing core is arranged parallel and spaced with an air guiding hole and a liquid guiding hole which are parallelly spaced, the air guiding tube and the liquid suction tube are respectively inserted into the air guiding hole and the liquid guiding hole, the air guiding tube is connected to the air pump, and the liquid suction tube is connected to the liquid suction tube; or the atomizing base is provided with a convex air guiding tube, the atomizing core is provided with an air guiding hole, the air guiding tube is inserted into the air guiding hole, the air guiding tube is connected to the air pump, and the atomizing core is further connected to the liquid suction tube.

Preferably, the atomizer further includes an atomizing cover, the atomizing cover including a first cover assembly and a second cover assembly, the first cover assembly and the second cover assembly being connected to each other to form the atomizing chamber, and the atomizing core and the atomizing base are both located in the atomizing cover.

Preferably, a baffle is further disposed in the atomizing chamber, the baffle is fixed in the atomizing chamber, and the baffle is located at the lower portion of the mist outlet;

a gap is pre-set between the baffle and the inner wall of the atomizing chamber; and/or, the baffle is provided with a mist hole.

Preferably, a bottle stopper is fixed to a bottle mouth of the liquid storage bottle, the pipe runs through the bottle stopper and protrudes from the upper surface of the bottle stopper, the atomizing base is formed with a pipe connection joint, and the pipe connection joint is connected to a portion of the pipe protruding from the bottle stopper.

Preferably, the atomizer further includes an atomizing cover, the atomizing base is connected to the atomizing cover, the atomizing chamber is formed in the atomizing cover or between the atomizing cover and the atomizing base, the atomizing cover is formed with the mist outlet, and the atomizing core is located in the atomizing chamber.

Preferably, an atomizing connection joint is formed on the atomizing cover, and the atomizing connection joint is connected to the air pump, a connecting post is formed on the atomizing base, the connecting post is detachably inserted into the atomizing cover to fix the atomizing base in the atomizing cover, the connecting post is connected to the atomizing connection joint and the air guiding tube, a lower end of the atomizing cover is provided with a liquid storage bottle connector, and the liquid storage bottle is detachably connected with the liquid storage bottle connector; or an atomizing connection joint is formed on the atomizing base, the atomizing connection joint is connected to the air pump, the air guide tube is connected to the atomizing connection joint, a lower end of the atomizing base is provided with a liquid storage bottle connector, and the liquid storage bottle is detachably connected with the liquid storage bottle connector.

Preferably, the connecting post extends upward relative to the liquid storage bottle, and an axial direction of the connecting post forms an angle of 20-70 degrees with an axial direction of the air guiding tube.

Preferably, an atomizing connection joint is formed on the atomizing cover or the atomizing base, and the atomizing connection joint is connected to the air pump, and the bottom wall of the atomizing connection joint is higher than the gas outlet.

Preferably, a balance vent that communicates with the atomizing chamber is also formed on the atomizing cover.

Preferably, the scent diffusion device further includes a power source and a driving circuit, the driving circuit is connected to the air pump, the power source supplies power to the air pump through the driving circuit, and the power source is a dry battery;

the driving circuit includes a first stage boosting circuit that boosts the power supply, an energy storage circuit that receives the output of the first stage boosting circuit, and a second stage boosting circuit for boosting the energy storage circuit; the power source is boosted by the first stage boosting circuit, outputted to the energy storage circuit, and charged to the energy storage circuit; and the second stage boosting circuit boosts the voltage of the energy storage circuit to cause the energy storage circuit to supply power to the load.

Preferably, the air pump intermittently operates, when the air pump stops working, the power source charges the energy storage circuit through the first stage boosting circuit, and when the air pump is in operation, the energy storage circuit is boosted by the second stage boosting circuit to supply power to the air pump.

Preferably, the driving circuit further includes a switching circuit that controls its switching by a control signal CTRL; one end of the switch circuit is connected to the output end of the energy storage circuit, and the other end of the switch circuit is connected to the input end of the second stage boost circuit; and the switching circuit controls conduction and disconnection of the second stage boosting circuit and the energy storage circuit.

Preferably, when the load is working, the switch circuit controls the second stage boosting circuit to be turned on with the energy storage circuit, otherwise the second stage boosting circuit is disconnected from the energy storage circuit.

Preferably, the energy storage circuit includes a super capacitor C1 or a rechargeable battery.

The other end of the liquid passage of the atomizing core of the embodiment of the present invention shrinks to form a liquid outlet, so the liquid passage does not need to be too thin. As long as the outlet is small enough to save the essential oil and spray a sufficiently fine spray, the gas passage uses the same principle as the liquid passage, which reduces the difficulty of processing. In addition, the widened liquid passage can also reduce the possibility of blockage.

BRIEF DESCRIPTION OF THE DRAWINGS

The above and other objects, features and advantages of the present invention will become more apparent from the detailed description of the invention. The same reference numerals are used throughout the drawings to refer to the same parts, and the drawings are not intended to be scaled to the actual size, and the emphasis is on the subject matter.

DETAILED DESCRIPTION OF PREFERRED EMBODIMENTS

Figure 1:
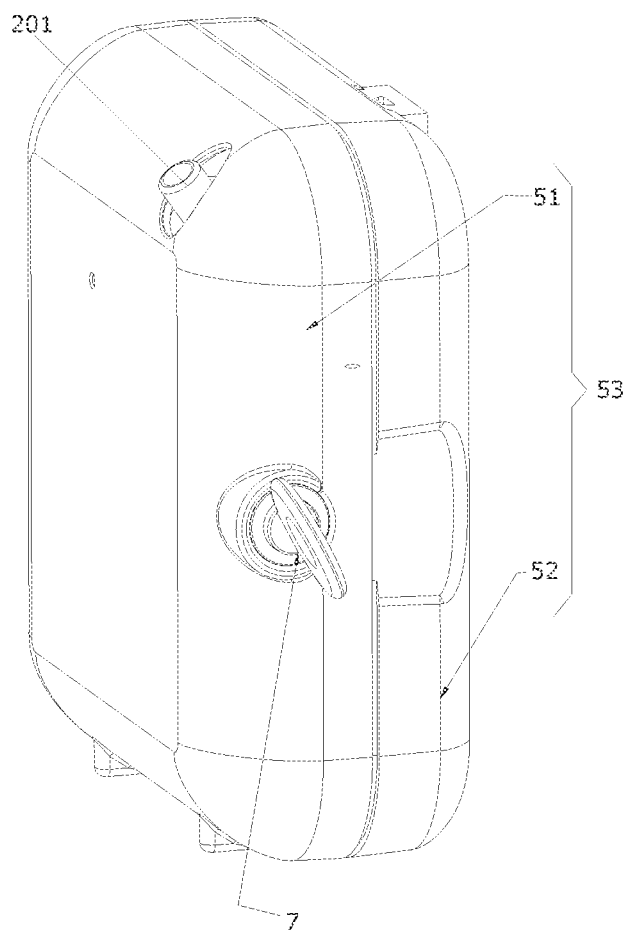
FIG. 1 is an overall structural view of a scent diffusion device according to a preferred embodiment of the present invention.

The technical solutions of the present invention are further described in detail below with reference to the accompanying drawings and specific embodiments. The present invention can be better understood and implemented by those skilled in the art, but the embodiments are not intended to limit the present invention.

As shown in FIGS. 1-29, the embodiment of the present invention provides a scent diffusion device including an air pump 3, an atomizer 2 and a liquid storage bottle 1, and the atomizer 2 is connected with the air pump 3 and the liquid storage bottle 1. Referring to FIG. 5, FIG. 12, FIG. 14 and FIG. 15, an atomizing chamber 20 is disposed in the atomizer 2, and a gas passage 21 and a liquid passage 22 are disposed in the atomizer 2. One end of the gas passage 21 communicates with the air pump 3 through the vent line 31, and the other end contracts to form the gas outlet 211. As long as the gas outlet 211 of the gas passage 21 is sufficiently small, the entire gas passage 21 is not required to be sufficiently thin, which reduces the manufacturing difficulty. One end of the liquid passage 22 communicates with the inside of the liquid storage bottle 1 through the pipe 11, and the other end contracts to form a liquid outlet 221. As long as the liquid outlet 221 of the liquid passage 22 is sufficiently small, the entire liquid passage 22 is not required to be sufficiently thin, which further reduces the manufacturing difficulty. At the same time, with respect to the prior art, since the transverse section of the liquid passage 22 is sufficiently large, the liquid essential oil can smoothly flow in the liquid passage 22, effectively reducing the probability of the liquid passage 22 being blocked. The gas outlet 211 is located on one side of the liquid outlet 221 and blows from the side of the liquid outlet 221 to the other side of the liquid outlet 221, and the liquid in the liquid storage bottle 1 is atomized by the principle of siphon. The atomizing chamber 20 is connected to the gas outlet 211 and the liquid outlet 221, and the atomizer 2 is further provided with a mist outlet 201 communicating with the atomizing chamber 20, the atomized mist passes through the atomizing chamber 20 and diffuses from the mist outlet 201 into the air. When the mist passes through the atomizing chamber 20, the larger droplets of the particles fall into the atomizing chamber 20 due to the action of gravity, and the fine mist diffuses from the mist outlet 201 into the air. In the prior art, many of the scent diffusion devices are not provided with the atomizing chamber 20, and the mist after atomization directly diffuses into the air. The mist droplets with larger particles in the mist will drip on the peripheral side of the scent diffusion device, contaminating the scent diffusion device and the surrounding environment, and the setting of the atomizing chamber 20 effectively alleviates this state.

In a preferred embodiment, the ratio of the maximum inner diameter of the end of the gas passage 21 to the vent line 31 to the inner diameter of the gas outlet 211 is greater than 3, and in the preferred embodiment, between 5 and 20, the gas passage 21 is easily formed and has excellent performance. The ratio of the maximum inner diameter of the end of the liquid passage 22 to the pipe 11 to the inner diameter of the liquid outlet 221 is greater than 3, and in the preferred embodiment is between 5 and 20, so that the liquid passage 22 is easily formed and has excellent performance. The atomizer 2 is easy to manufacture, the power requirement of the air pump 3 is also lower, and the mist is more delicate, and the liquid passage 22 and the gas passage 21 are not easily blocked.

In a preferred embodiment, the bottom wall of at least a portion of the vent line 31 is positioned above the gas outlet 211 to prevent liquid essential oil from flowing back to the air pump 3, affecting the performance and service life of the air pump 3. The mist outlet 201 is inclined from the inside to the outside with respect to the liquid storage bottle 1. Under the action of gravity, the larger droplets of the particles can flow back to the atomizing chamber 20 along the mist outlet 201.

Figure 13:
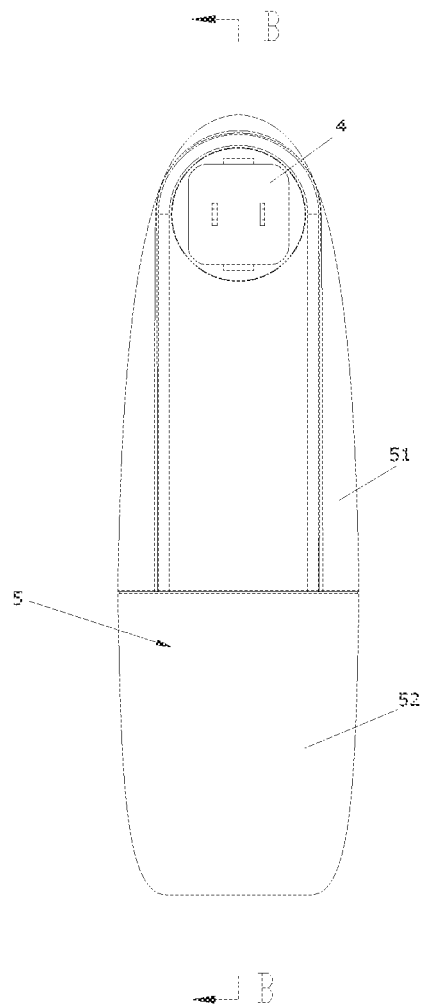
FIG. 13 is a rear elevational view of another preferred embodiment of the present invention.
Figure 14:
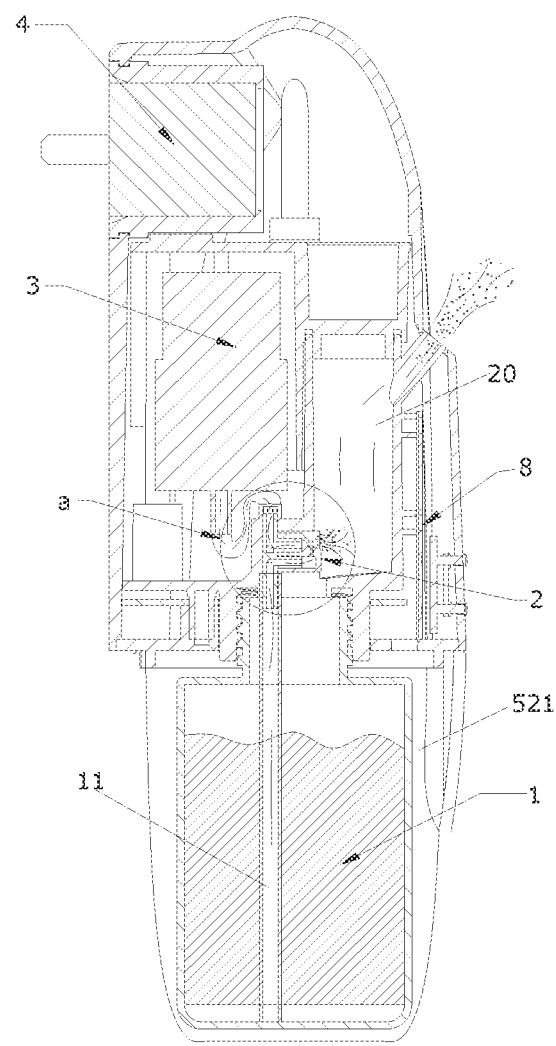
FIG. 14 is a cross-sectional view taken along line BB of FIG. 13.
Figure 15:
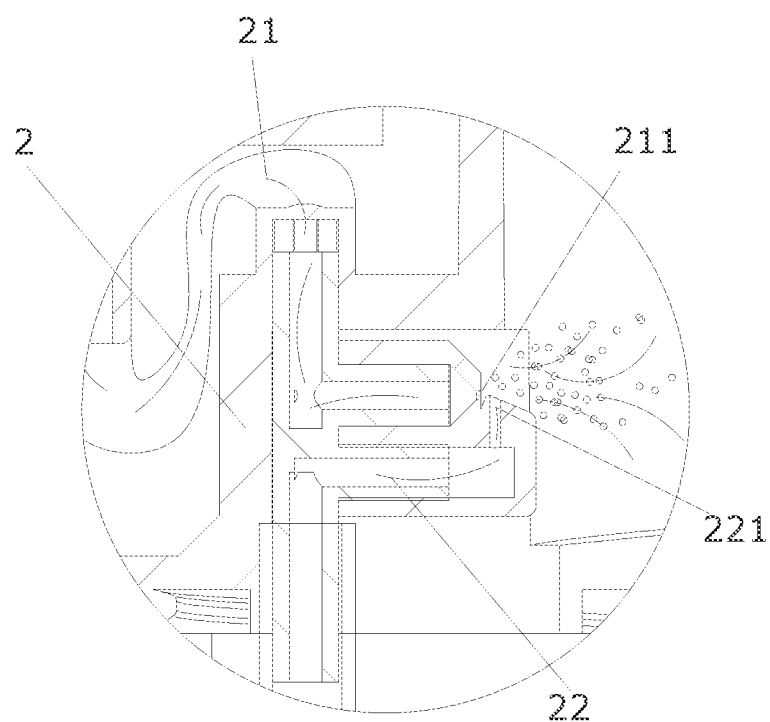
FIG. 15 is an enlarged view of a portion of FIG. 14.

Referring to FIGS. 13 and 14, in a preferred embodiment, the scent diffusion device further includes a power plug 4 and a housing 5, and the liquid storage bottle 1, the atomizer 2 and the air pump 3 are located inside the housing 5, so that the appearance thereof is more beautiful. At the same time, a layer of protection is formed to make the expansion device more durable, and the housing 5 can also block a part of the noise. The mist outlet 201 is exposed from the housing 5, and the plug end of the power plug 4 protrudes outside the housing 5, facilitating the direct insertion of the power plug 4 into the socket. The other end of the power plug 4 is fixedly connected to the housing 5 via a plug base 41, and the power plug 4 is integrated with the housing 5. When the power plug 4 is inserted into the socket on the wall, the entire scent diffusion device is also fixed on the socket, and there is no need to separately locate the scent diffusion device, which saves space and is simpler to operate. The power plug 4 is electrically connected to the air pump 3, and the power plug 4 supplies electric energy to the air pump 3. The insertion direction of the power plug 4 may be substantially perpendicular to the axial direction of the liquid storage bottle 1.

In a further preferred embodiment, the mist outlet 201 is disposed on the other side of the housing 5 opposite the power plug 4, and charging does not affect the use of the scent diffusion device.

Figure 3:
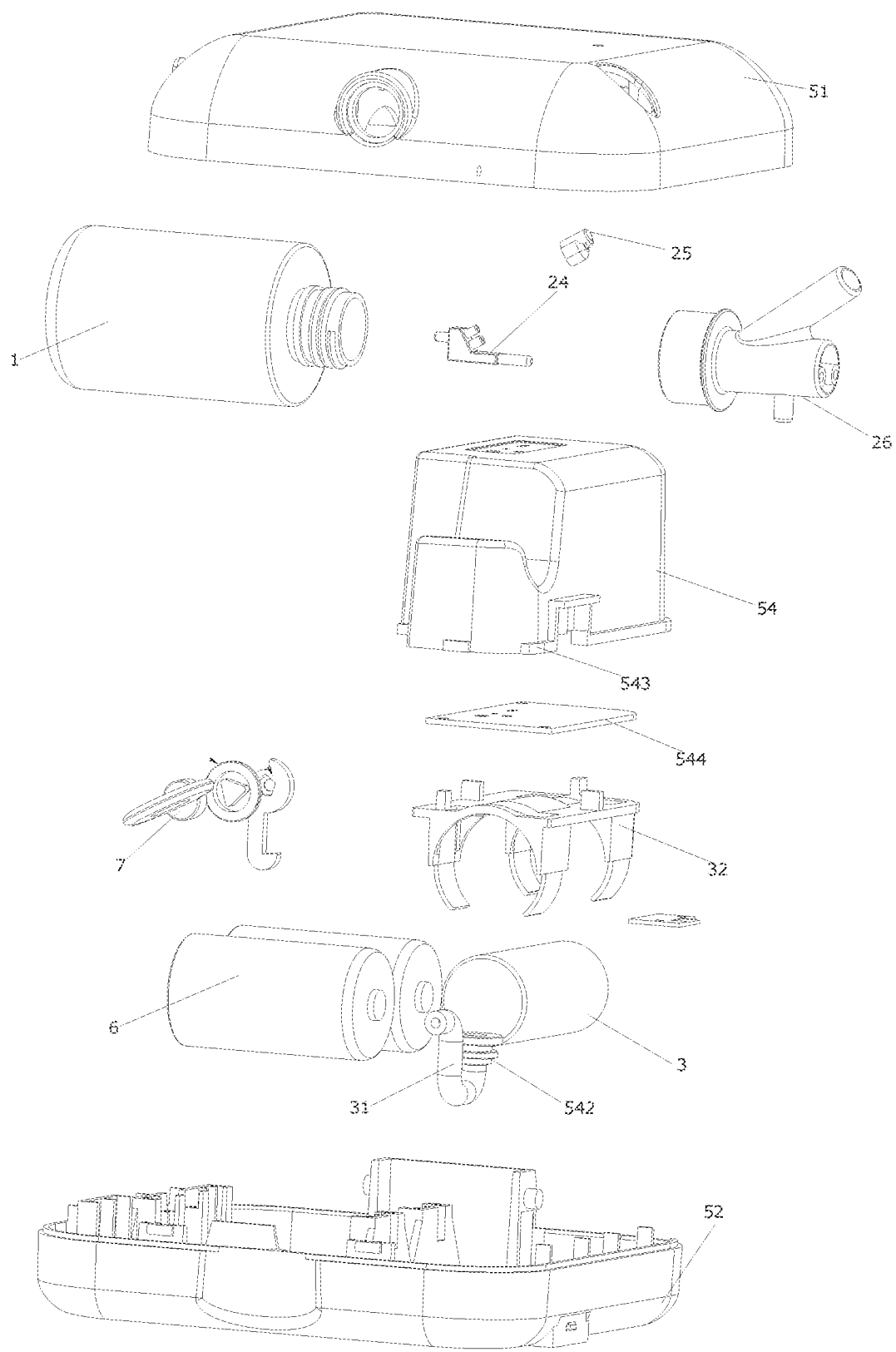
FIG. 3 is an exploded view of the scent diffusion device of the preferred embodiment of the present invention.
Figure 4:
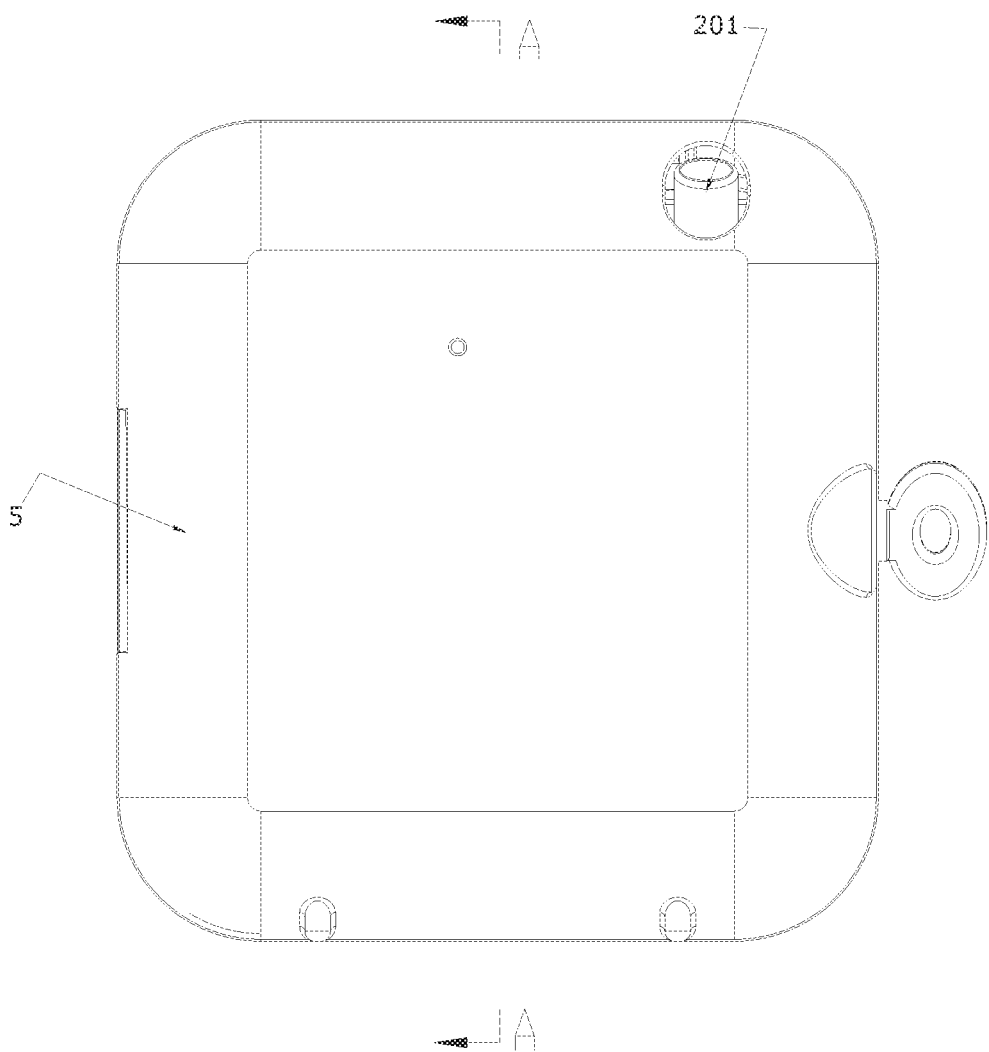
FIG. 4 is a front elevational view of the scent diffusion device of the preferred embodiment of the present invention.
Figure 16:
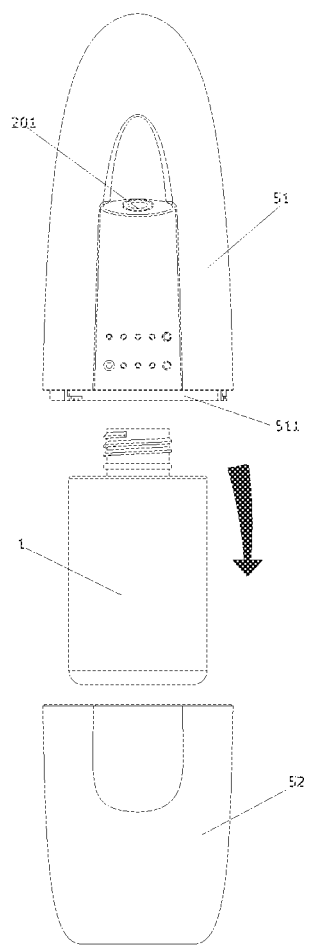
FIG. 16 is an exploded view of another preferred embodiment of the present invention.
Figure 17:
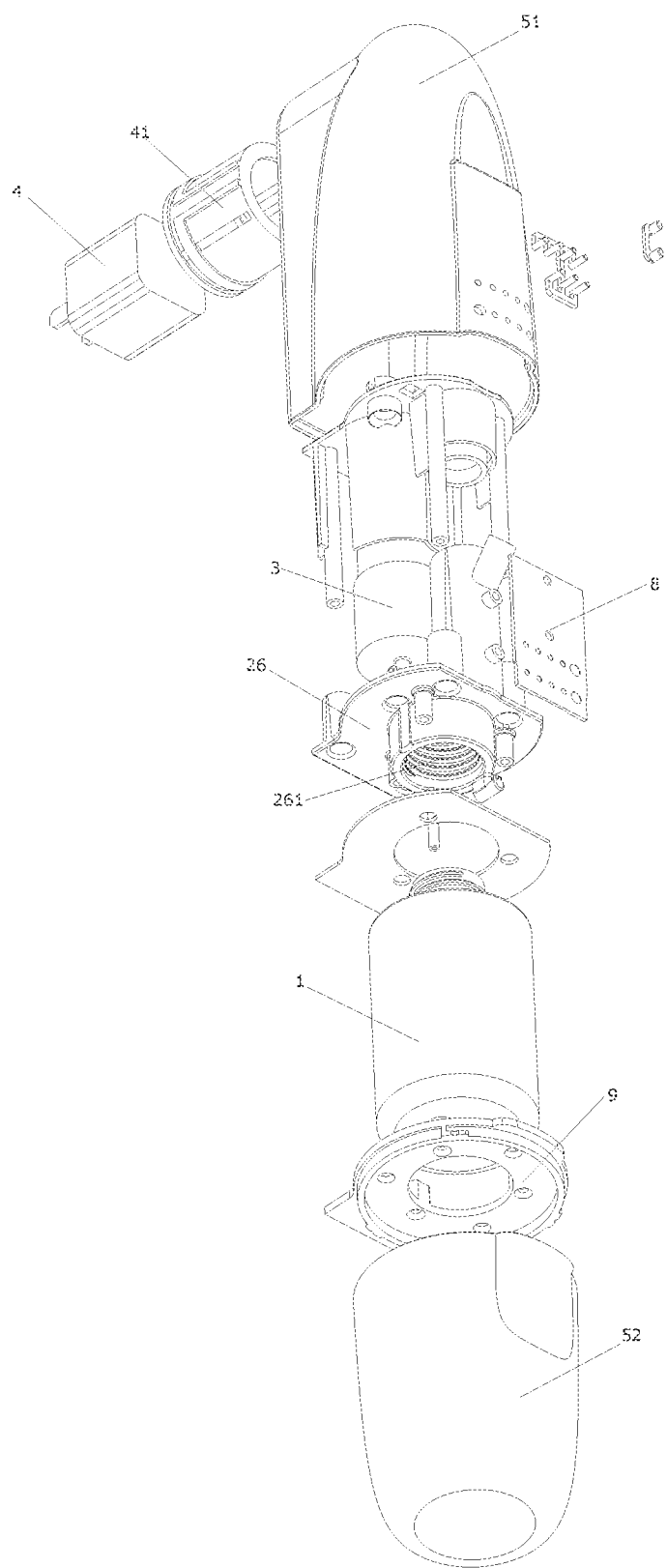
FIG. 17 is a further exploded view of another preferred embodiment of the present invention.
Figure 18:
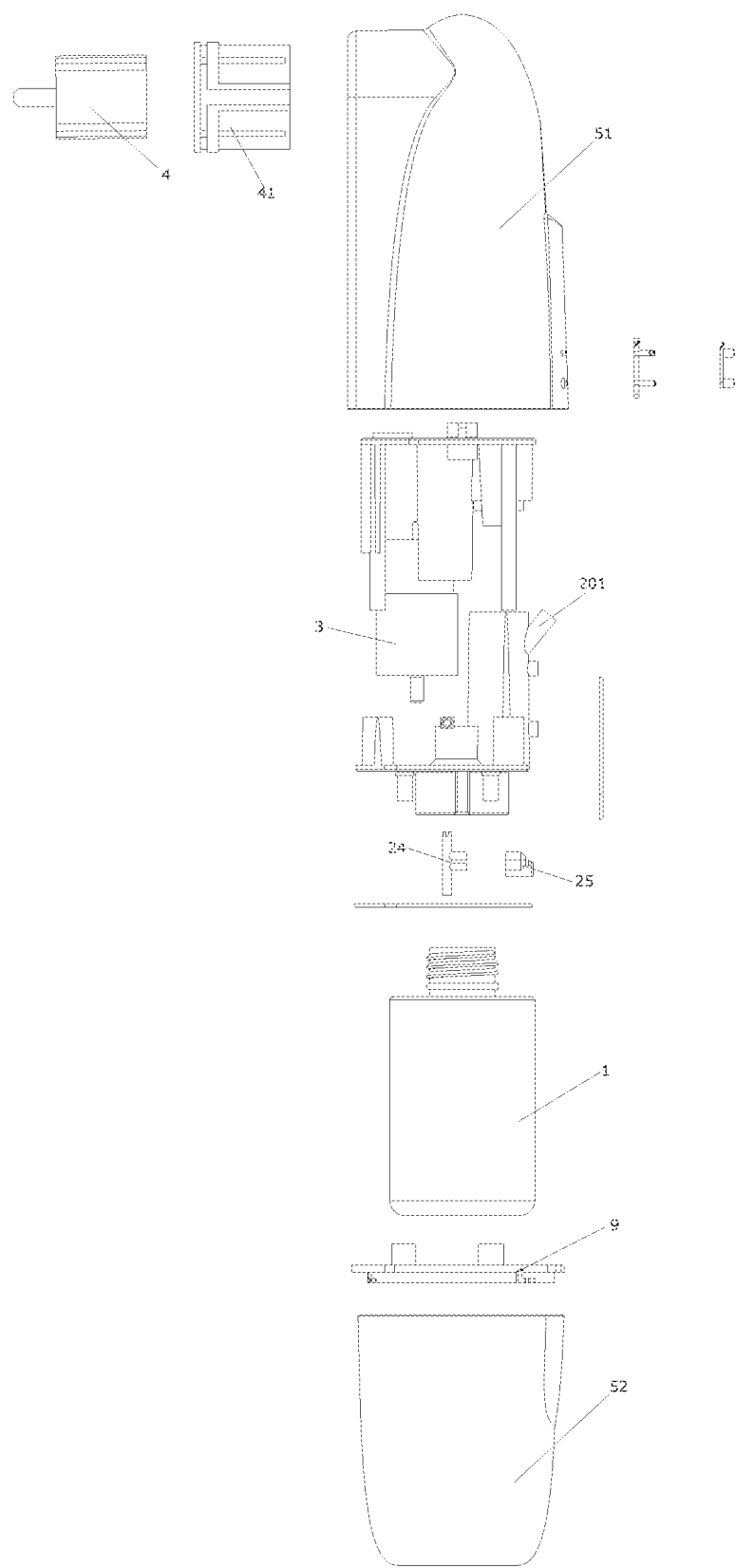
FIG. 18 is a front elevational view of a further exploded view of another preferred embodiment of the present invention.
Figure 19:
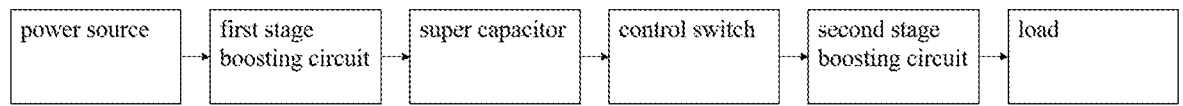
FIG. 19 is a schematic block diagram of a driving circuit according to an embodiment of the present invention.

Referring to FIGS. 3 and 16, in a further preferred embodiment, the housing 5 includes an upper housing 51 and a lower housing 52, and the upper housing 51 and the lower housing 52 are detachably connected, and the air pump 3 and the atomizer 2 are disposed in the upper housing 51, which is convenient for production and manufacture, and can also reduce noise generated by the air pump 3. The power plug 4 is fixed on the upper housing 51, and the upper housing 51 is provided with a connecting portion 511, and the liquid storage bottle 1 is screwed with the connecting portion 511 to facilitate the disassembly of the liquid storage bottle 1, thereby replacing the liquid storage bottle 1 or adding essential oil to the liquid storage bottle 1. The lower housing 52 is provided with a receiving chamber 521, and the liquid storage bottle 1 is housed in the receiving chamber 521 to protect the liquid storage bottle 1. A lower portion of the liquid storage bottle 1 and a base 9 are also disposed in the housing 5. The base 9 can also function to cushion shock absorption, effectively reducing the noise generated by the air pump 3 and the atomizing core 25.

Referring to FIG. 3, in a preferred embodiment, the scent diffusion device further includes an outer housing 53 and an inner housing 54, which is mounted in the outer housing 53 and detachably coupled to the inner wall of the outer housing 53. The inner housing 54 is formed with an air pump installation chamber 541, and the air pump 3 is installed in the air pump installation chamber 541. This arrangement makes the scent diffusion device more modular, simpler to manufacture, and lower in cost. Further, an inner portion of the inner housing 54 is provided with an air pump holder 32, and the air pump holder 32 is fixedly coupled to the inner housing 54, and the air pump 3 is fixed in the inner housing 54 by the air pump holder 32. A circuit board connected to the air pump 3 may also be disposed in the inner housing 54 to make the structure of the scent diffusion device more compact. The inner housing 54 is further provided with an air pump connection joint 33, and the air pump connection joint 33 is connected to the air pump 3 through the vent line 31, and the vent line 31 and the air pump connection head 542 are more easily connected. The atomizer 2 and the liquid storage bottle 1 are mounted in the outer housing 53 and located outside the inner housing 54, and the removal of the inner housing 54 does not affect the atomizer 2 and the liquid storage bottle 1. The atomizer 2 is provided with an atomizing connection joint 23, and the atomizing connection joint 23 is in communication with the gas passage 21, and the atomizing connection joint 23 is plugged and sealed with the air pump connection joint 33 to avoid air leakage and facilitate production.

Figure 2:
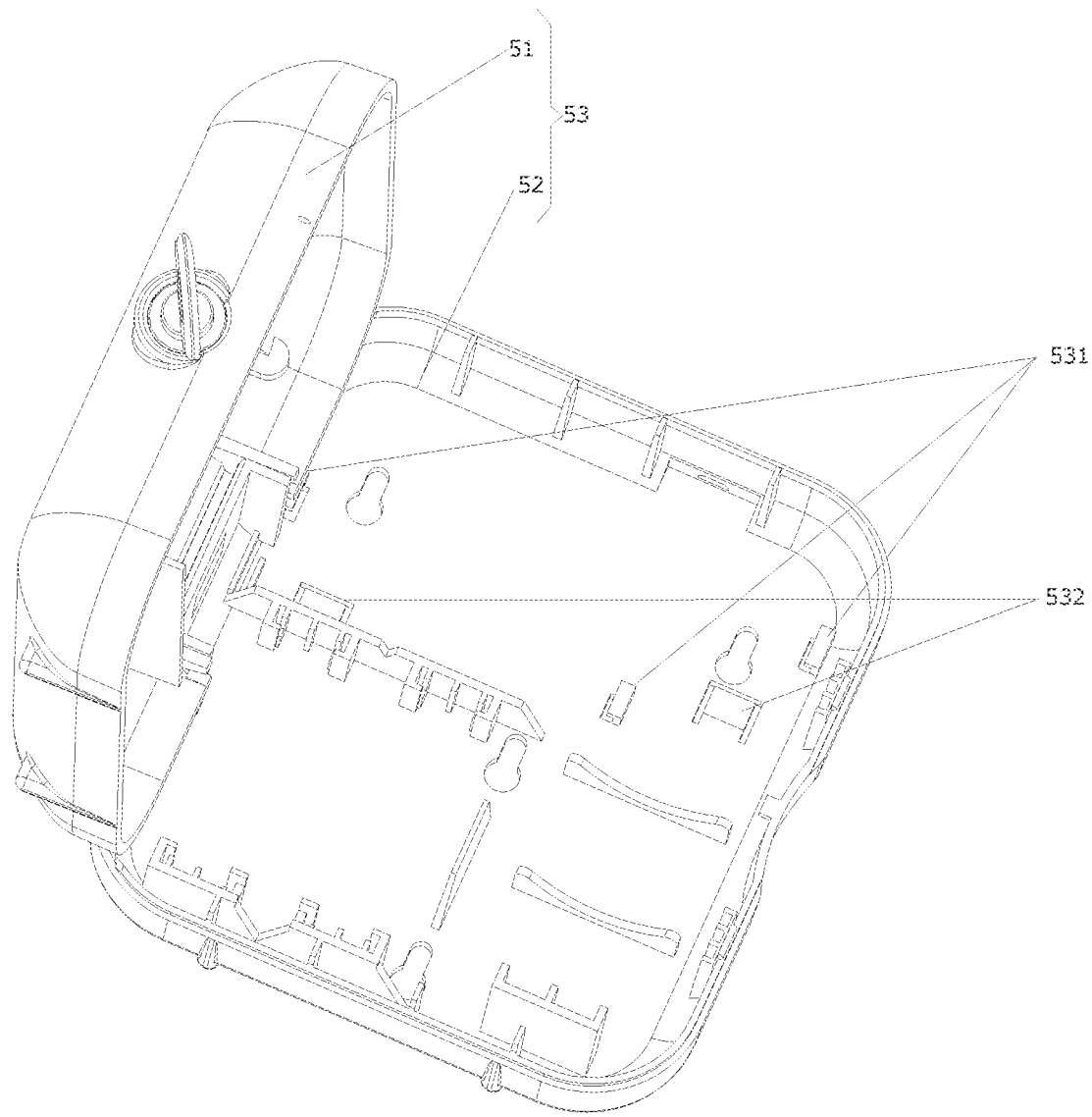
FIG. 2 is an internal structural view of an outer housing of a preferred embodiment of the present invention.
Figure 6:
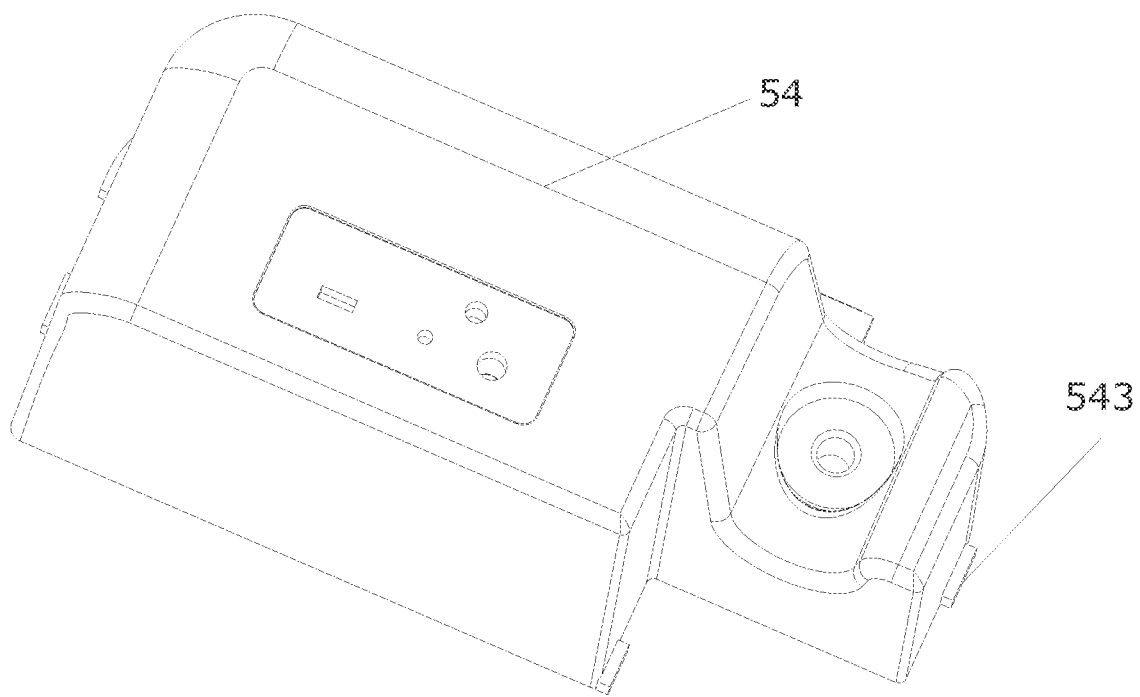
FIG. 6 is an overall structural view of an inner housing of a preferred embodiment of the present invention.

Referring to FIGS. 2 and 6, in a further preferred embodiment, the inner wall of the outer housing 53 is provided with a plurality of buckles 531, and the inner housing 54 is provided with a holder 543 that engages with the buckle 531, and the inner housing 54 is detachably connected to the inner wall of the outer housing 53 by the buckle 531 and the holder 543. It is more convenient to disassemble the inner housing 54, so that the air pump 3 fixed to the inner housing 54 can be mounted in any of the aerosol dispensers provided with the buckle 531, which is more versatile. A limiting member 532 is further disposed on the inner wall of the outer housing 53. The limiting member 532 is an elastic member, and the limiting member 532 abuts against the outer wall of the inner housing 54. The limiting member 532 is located on one side of the inner housing 54 fixed to the outer housing 53, and the limiting member 532 is fixedly coupled to the outer housing 53. When the inner housing 54 is installed, the inner housing 54 presses the limiting member 532. When the inner housing 54 is installed in position, the inner housing 54 no longer presses the limiting member 532, and the limiting member 532 is ejected. When the limiting member 532 is ejected, a sound is emitted, and the limiting member 532 functions to remind the user of the installation condition and the limit position.

Referring to FIG. 3, in a preferred embodiment, the scent diffusion device further includes an outer housing 53 and an inner housing 54, and the inner housing 54 is mounted in the outer housing 53, and the inner housing 54 is formed with an air pump mounting chamber 541, and the air pump 3 is installed in the air pump mounting chamber 541. Further, an inner portion of the inner housing 54 is provided with an air pump holder 32, and the air pump holder is fixedly connected to the inner housing 54, and the air pump 3 is fixed in the inner housing 54 by the air pump holder 32. The inner housing 54 is further provided with an air pump connection joint 33, and the air pump connection joint 33 is connected to the air pump 3 through the vent line 31 for convenient connection. The atomizer 2 and the liquid storage bottle 1 are mounted in the outer housing 53 and located outside the inner housing 54, and the removal of the inner housing 54 does not affect the atomizer 2 and the liquid storage bottle 1. The atomizer is provided with an atomizing connection joint, and the atomizing connection joint is connected with the gas passage. The air pump connection joint 33 is made of a silicone material, and the atomizing connection joint 23 is inserted into the air pump connection joint 33, and is sealed and matched with the air pump connection joint 33. The air pump connection joint 33 of the silica gel is used to replace the plastic conversion head with a sealing ring in the prior art, so that the connection between the ventilation duct 31 and the air pump 30 is more convenient, and the sealing effect is better. And the air pump connection joint 33 of the silicone is more durable than the seal ring. The inner housing 54 is further provided with a PCB board 544. The PCB board 544, the air pump 3 and the air pump connection joint 33 and the like are mounted on the inner housing 34 to form an inner housing assembly, and the inner housing assembly is integral. When developing products for different customers, it is only necessary to reserve the mounting position of the lower inner housing assembly and the buckle 531 holding the inner housing assembly, and it is not necessary to redesign the components located on the inner housing assembly. Therefore, the workload is reduced, and production is more convenient. In a preferred embodiment, the atomizer 2 includes an atomizing base 24 and an atomizing core 25, the atomizing base 24 is in communication with the air pump 3, and the atomizing core 25 is mounted on the atomizing base 24, both the gas outlet 211 and the liquid outlet 221 are disposed on the atomizing core 25.

In a further preferred embodiment, the atomizing core 25 is detachably coupled to the atomizing base 24, and the atomizing core 25 is integrally formed of a plastic material to facilitate manufacturing and installation.

Figure 7:
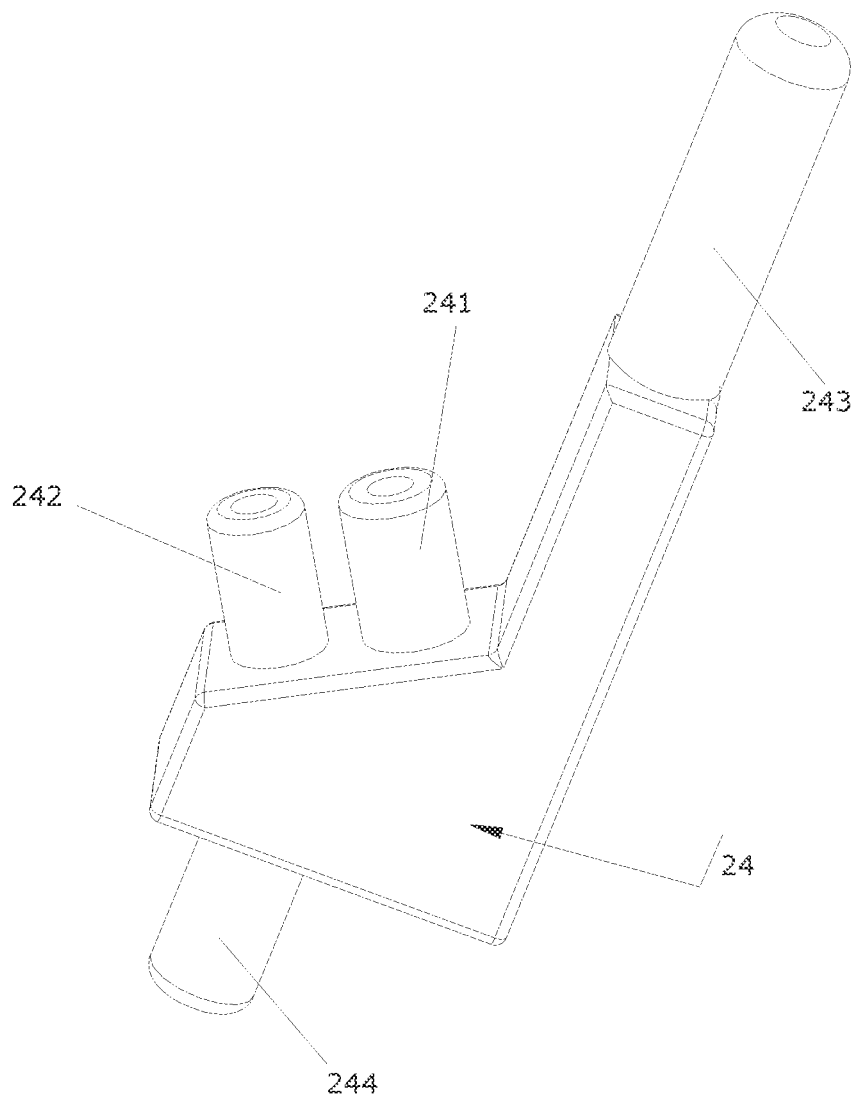
FIG. 7 is an overall structural view of an atomizing base according to a preferred embodiment of the present invention.
Figure 8:
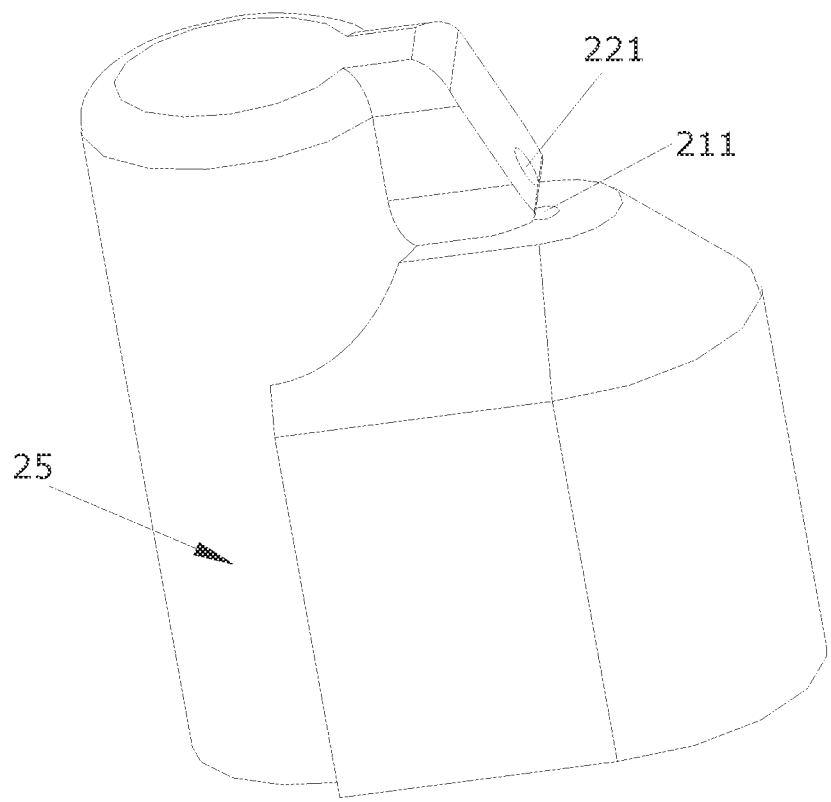
FIG. 8 is an overall structural view of an atomizing core according to a preferred embodiment of the present invention.
Figure 9:
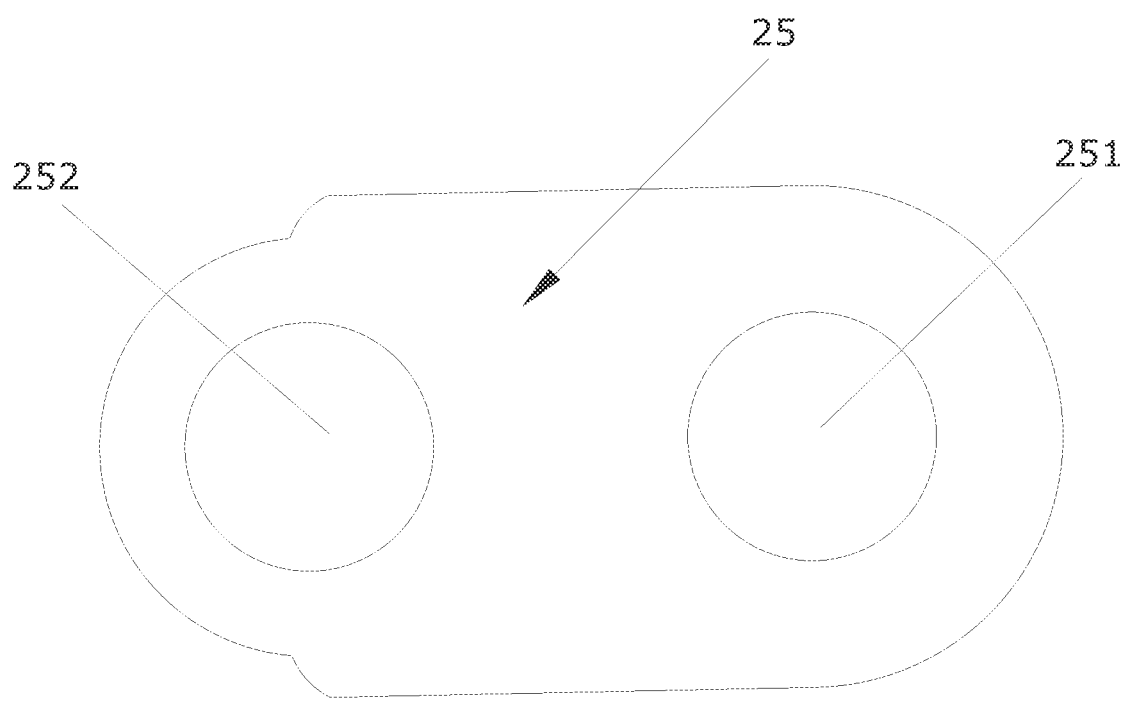
FIG. 9 is a bottom plan view of an atomizing core of a preferred embodiment of the present invention.

Referring to FIGS. 7, 8 and 9, in a further preferred embodiment, the atomizing base 24 is provided with a protruding air guiding tube 241 and a liquid suction tube 242. The air guiding tube 241 and the liquid suction tube 242 are arranged in parallel and spaced apart. The atomizing core 25 is parallel and spaced apart from the air guiding core 25 with an air guiding hole 251 and a liquid guiding hole 252. The air guiding tube 241 and the liquid suction tube 242 are respectively inserted into the air guiding hole 251 and the liquid guiding hole 252 to facilitate the insertion and fixation. The air guiding tube 241 is in communication with the air pump 3, and the liquid suction tube 242 is in communication with the pipe 11. In another preferred embodiment, the atomizing base 24 is provided with a convex air guiding tube 241, the atomizing core 25 is provided with an air guiding hole 251, the air guiding tube 241 is inserted into the air guiding hole 251, the air guiding tube 241 is in communication with the air pump 3, and the atomizing core 25 is also in communication with the pipe 11.

Figure 11:
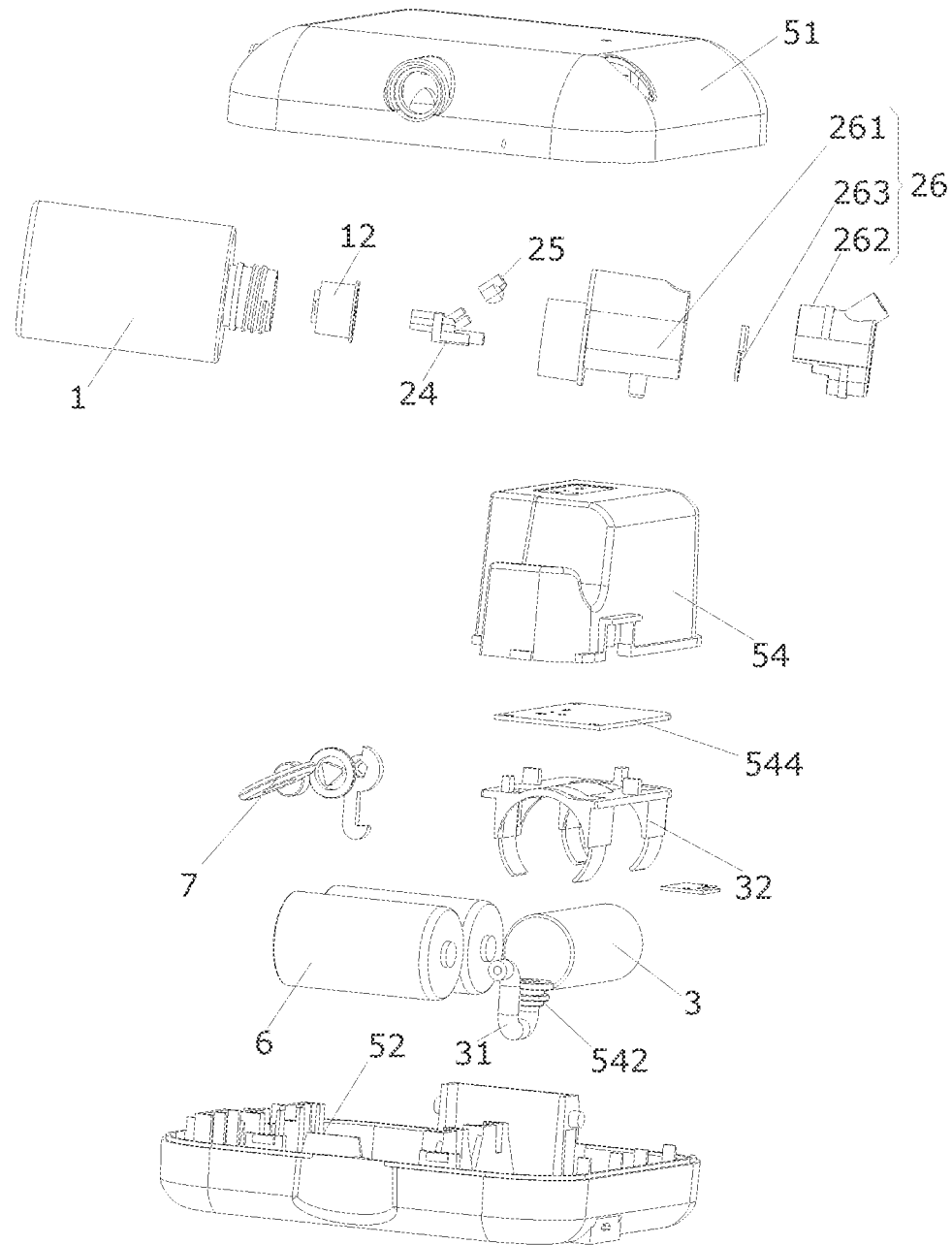
FIG. 11 is an exploded view of the scent diffusion device of another embodiment of the selected embodiment of the present invention.
Figure 12:
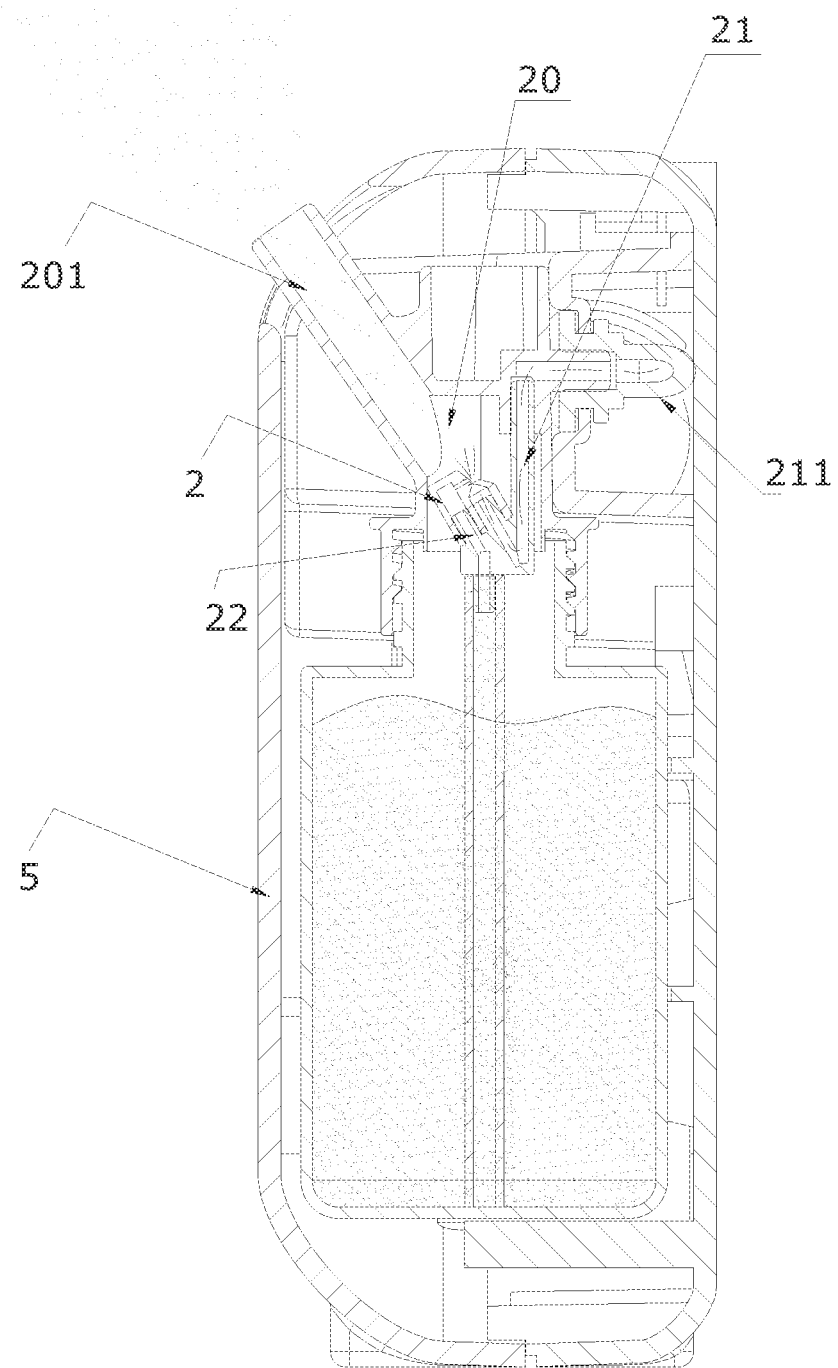
FIG. 12 is a cross-sectional view showing another aspect of the AA direction of FIG. 5.

Referring to FIGS. 11 and 12, in another aspect of the preferred embodiment, the atomizer 2 also includes an atomizing cover 26 that includes a first cover assembly 261 and a second cover assembly 262. The first cover assembly 261 and the second cover assembly 262 are detachably fixedly connected. Further, one end of the first cover assembly 261 and the second cover assembly 262 are openly disposed, one end of the second cover assembly 262 connected to the first cover assembly 261 is disposed in cooperation with the first cover assembly 261, and the second cover assembly 262 is inserted into the upper portion of the first assembly 261 and is fixedly engaged with the first cover assembly 261. The first cover assembly 261 and the second cover assembly 262 together form an atomizing chamber 20. The atomizing core 25 and the atomizing base 24 are both located in the atomizing cover 26, and the atomized essential oil from the atomizing core 25 is first sprayed in the atomizing chamber 20. The large particle mist falls in the atomizing chamber 20, and the fine mist diffuses from the mist outlet 201 into the air.

In a further preferred embodiment, a baffle 263 is further disposed within the atomizing chamber 20. Further, the baffle 263 is an aluminum sheet. The baffle 263 is fixed in the atomizing chamber 20, and the baffle 263 is located at a lower portion of the mist outlet 201. A gap is preset between the baffle 263 and the inner wall of the atomizing chamber 20; alternatively, the baffle 263 is provided with a through-hole, and the mist can pass through the baffle 263 to enter the mist outlet 201, before the mist enters the mist outlet 201, it is first necessary to pass through the baffle 263, and the droplets of the large particles are attached to the baffle 263, thereby further reducing the droplets of the large particles and making the mist from the mist outlet 201 more delicate.

In a further preferred embodiment, the bottle mouth of the liquid storage bottle 1 is fixed with a bottle stopper 12, which is a rubber stopper, and the bottle stopper 12 is interference-fitted with the bottle mouth to function to seal the bottle mouth of the liquid storage bottle 1. The pipe 11 extends through the bottle stopper 12 and protrudes from the upper surface of the bottle stopper 12, and the bottle stopper 12 functions to fix the pipe 11. A pipe connection joint 244 is formed on the atomizing base 24, and the pipe connection joint 244 is connected to a portion of the pipe protruding from the bottle stopper 12.

In a further preferred embodiment, the mist outlet 201 is disposed on the second cover assembly 262 and the mist outlet 201 is upwardly inclined. An atomizing cover 26 is provided with an atomizing connecting connector 23, and the atomizing connecting connector 23 is disposed on the first cover assembly 261. The portion of the second cover assembly 262 that is inserted into the first cover assembly 261 is located at an upper portion of the atomizing connection joint 23, and the second cover assembly 262 does not block the opening of the atomizing connection joint 23 on the side wall of the first cover assembly 261.

Figure 5:
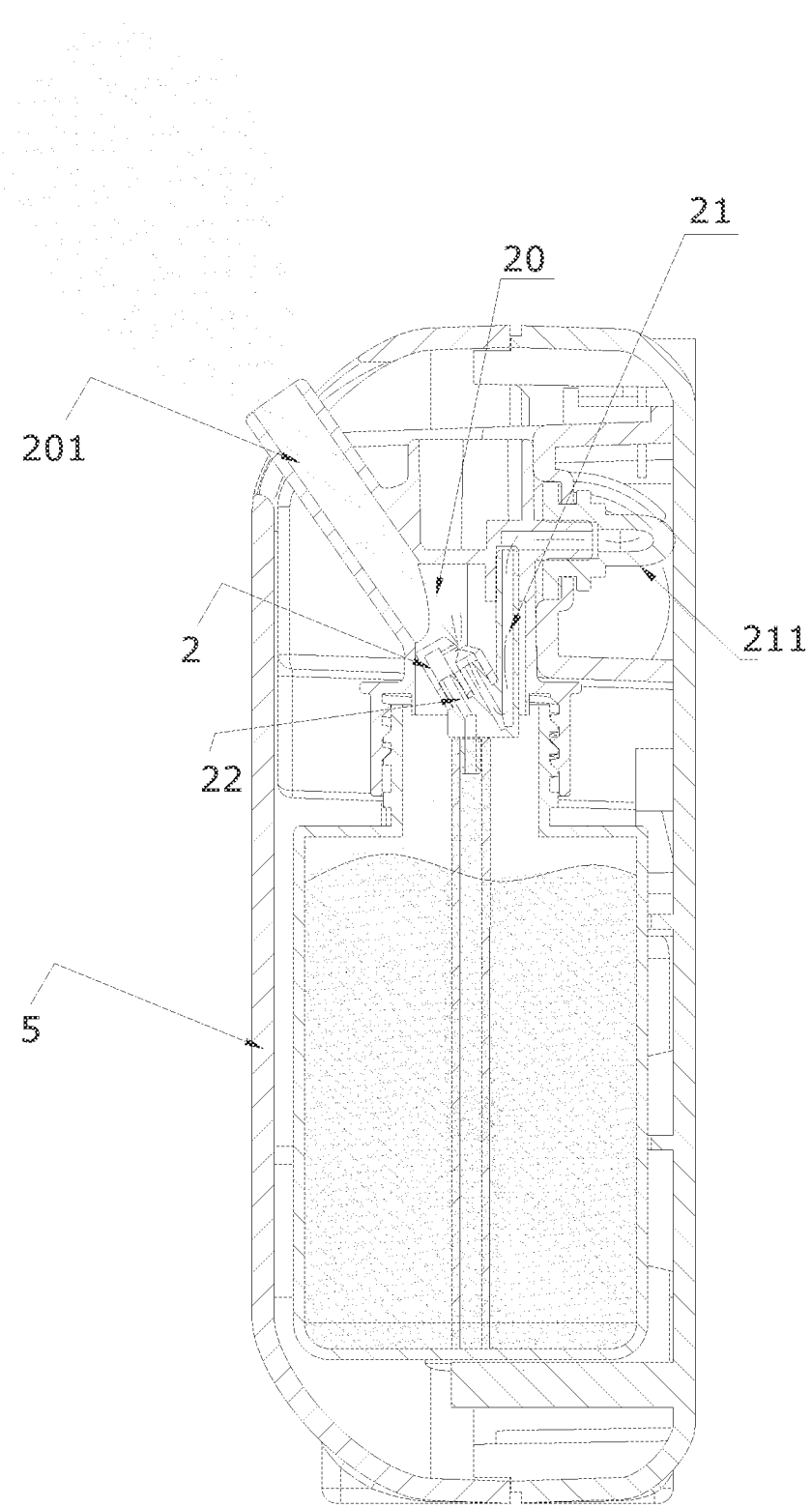
FIG. 5 is a cross-sectional view of the AA direction of FIG. 4.
Figure 10:
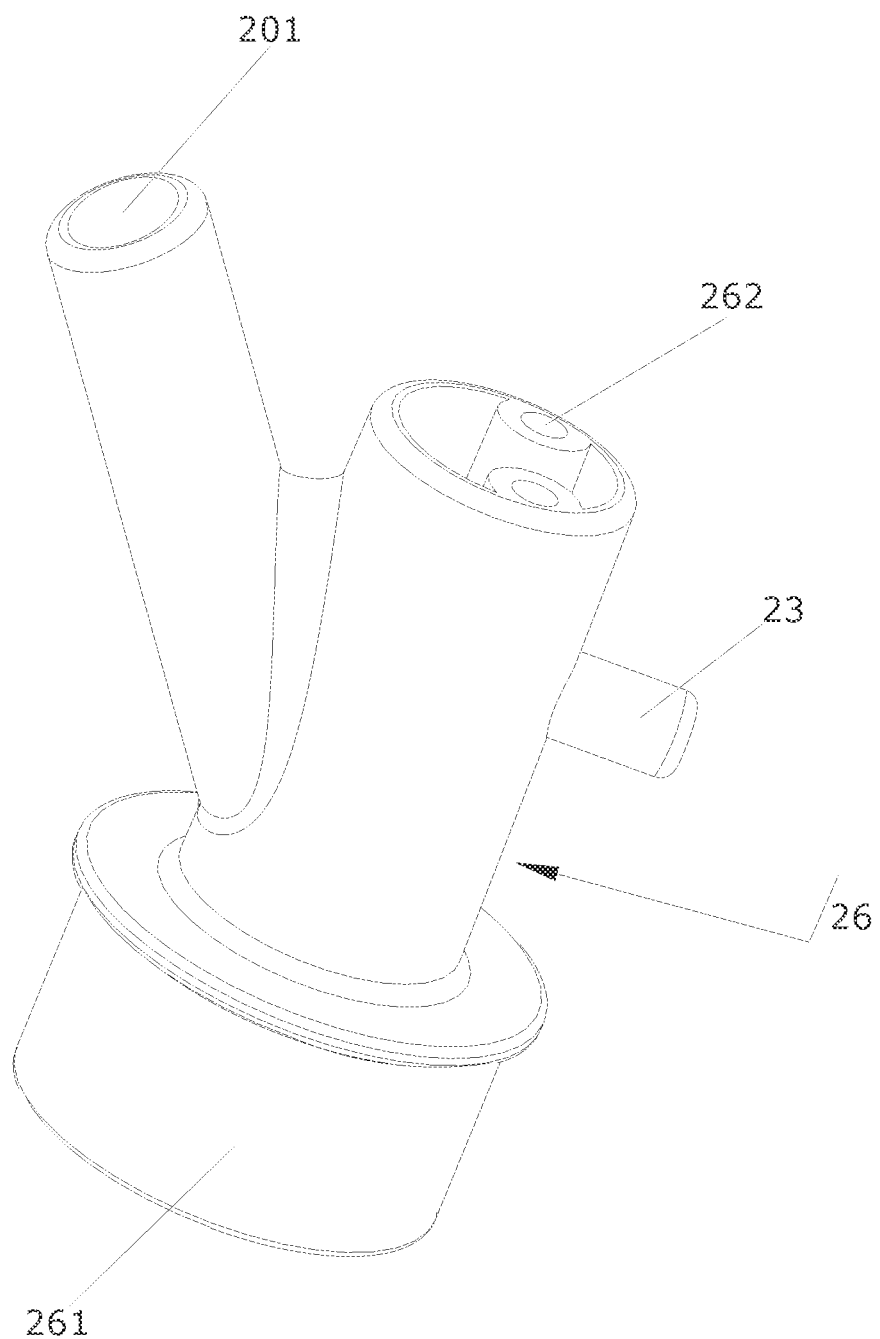
FIG. 10 is an overall structural view of an atomizing cover according to a preferred embodiment of the present invention.

Referring to FIGS. 5 and 10, in a preferred embodiment, the atomizer 2 further includes an atomizing cover 26, the atomizing base 24 is connected to the atomizing cover 26, an atomizing chamber 20 is formed in the atomizing cover 26 or between the atomizing cover 26 and the atomizing base 24, an atomizing port 201 is formed on the atomizing cover 26, and the atomizing core 25 is located in the atomizing chamber 20.

Referring to FIG. 10, in a further preferred embodiment, the atomizing cover 26 is formed with an atomizing connection joint 23 which is in communication with the air pump 3. A connecting post 243 is formed on the atomizing base 24, and the connecting post 243 is detachably inserted into the atomizing cover 26 to fix the atomizing base 24 in the atomizing cover 26. The connecting post 243 is connected to the atomizing connection joint 23 and the air guiding tube 241. The lower end of the atomizing cover 26 is provided with a liquid storage bottle connecting head 261, and the liquid storage bottle 1 is detachably connected with the liquid storage bottle connecting head 261. The connecting post 243 extends upward relative to the reservoir 1 and the axial direction of the connecting post 243 forms an angle of 20-70 degrees with the axial direction of the air guiding tube 241, which is preferably 30-60 degrees. In another preferred embodiment, the atomizing base 24 is formed with an atomizing connection joint 23 and a pipe connection joint 244, and the atomizing connection joint 23 is in communication with the air pump 3, the air guiding tube 241 is in communication with the atomizing connection joint 23, and the lower end of the atomizing base 24 is provided with a liquid storage bottle connecting head 261, and the liquid storage bottle 1 and the pipe connection joint 244 are detachably connected.

In a further preferred embodiment, an atomizing connection joint 23 is formed on the atomizing cover 26 or the atomizing base 24, and the atomizing connection joint 23 communicates with the air pump 3, and the bottom wall of the atomizing connection joint 23 is higher than the gas outlet port 211 to prevent the liquid essential oil from flowing back.

Referring to FIG. 10, in a further preferred embodiment, the atomizing cover 26 is also formed with a balanced vent 262 that communicates with the atomizing chamber 20 to prevent unbalanced air pressure within the atomizing chamber 20.

In a preferred embodiment, the gas passage 21 is composed of an atomizing connection joint 23 of the atomizing cover 26, a connecting post 243 of the atomizing base 24, an air guiding tube 241, an air guiding hole 251 of the atomizing core 25, and a gas outlet 211 located on the atomizing core 25 and communicating with the air guiding hole 251. The liquid passage 22 is composed of a pipe 11, a pipe connection joint 244 and a liquid suction tube 242 of the atomizing base 24, a liquid guiding hole 252 of the atomizing core 25, and a liquid outlet 211 located on the atomizing core 25 and communicating with the liquid guiding hole 252.

In a preferred embodiment, the lower housing 52 is hinged to one side of the upper housing 51, and the other side of the lower housing 52 and the upper housing 51 is provided with a lock body 7. The lock body 7 can be a lock body 7 that is opened using a key or can be a code lock. When the scent diffusion device is used in a public place, it is possible to prevent the person from damaging the scent diffusion device, and also to prevent the power source 6 and the liquid storage bottle 1 from falling out of the outer housing 53.

Figure 20:
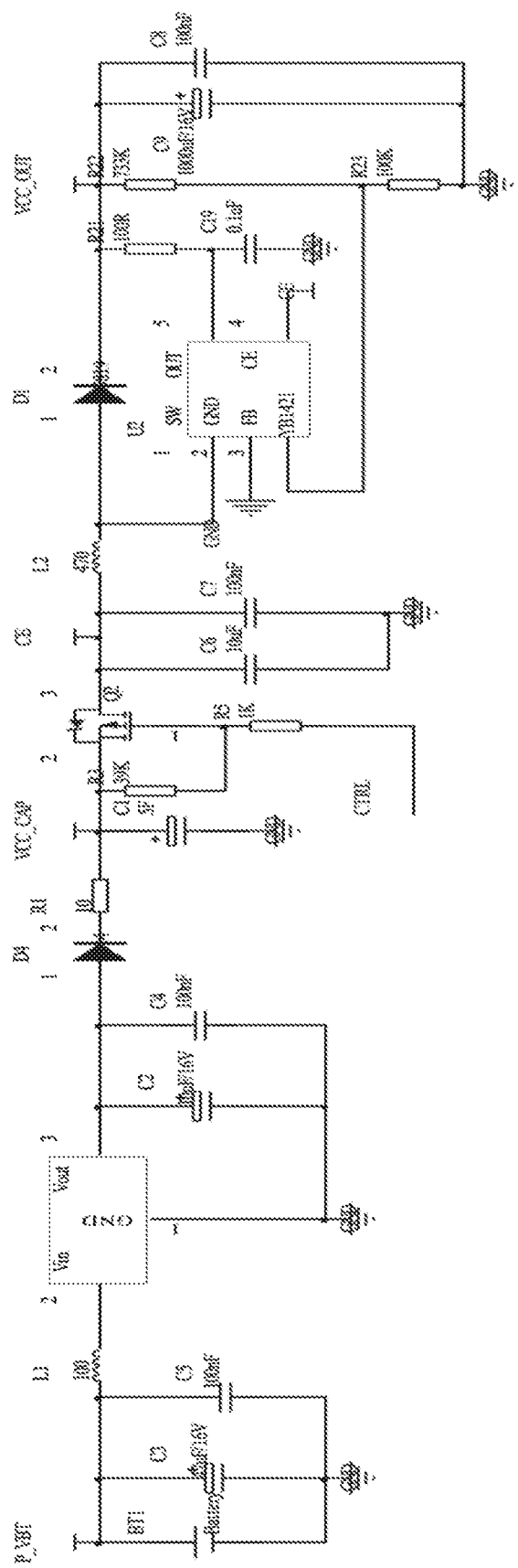
FIG. 20 is a circuit diagram of a driving circuit according to an embodiment of the present invention.

Referring to FIGS. 19-24, in a preferred embodiment, the scent diffusion device further includes a power source 6 and a driving circuit. The driving circuit is connected to the air pump 3. The power source 6 supplies power to the air pump 3 through a driving circuit, and the power source 6 is a dry battery. The driving circuit includes a first stage boosting circuit that boosts the power source 6, a storage circuit that receives the output of the first stage boosting circuit, and a second stage boosting circuit that boosts the energy storage circuit. In the present embodiment, the power source 6 is a dry battery, and the load is an air pump 3 of an essential oil atomization spreader. In other embodiments, the power source 6 can also select other portable power sources 6 such as batteries, and the load can be other intermittently working devices. After the power supply 6 is boosted by the first stage booster circuit, it is output to the energy storage circuit and charges the energy storage circuit; the second stage boost circuit boosts the voltage of the energy storage circuit to supply the load to the load. Referring to FIG. 20, the input end of the first stage boosting circuit is connected to the power supply and amplifies the voltage of the power supply, and the output end is connected to the input end of the energy storage circuit and charges the energy storage circuit. The input end of the second stage boost circuit is connected to the output end of the energy storage circuit through the switch circuit and amplifies the voltage at the output end of the energy storage circuit. The output end of the second stage boost circuit is electrically connected to the load and supplies power to the load. The first stage boosting circuit, the energy storage circuit, and the second stage boosting circuit are all unidirectional circuits. After the power source 6 is boosted by the first stage booster circuit, it is output to the energy storage circuit and charges the energy storage circuit. When the power of the energy storage circuit reaches the preset power, the second stage boost circuit is turned on and the voltage of the energy storage circuit is boosted, so that the energy storage circuit supplies power to the load. It should be noted that the term "energy storage circuit supplies power to the load" may be direct power supply or indirect power supply. For example, in other embodiments, the driving circuit may further include a third stage boosting circuit (not shown) and a secondary energy storage circuit. The secondary storage circuit is connected to the second stage boost circuit, and the third stage boost circuit is connected to the secondary storage circuit. The electric energy of the energy storage circuit is boosted by the second stage boosting circuit, output to the secondary energy storage circuit, and the secondary energy storage circuit is charged. The third stage boost circuit boosts the voltage of the energy storage circuit to cause the secondary energy storage circuit to supply power to the load. In this embodiment, although the energy storage circuit is indirectly supplying power to the load, it is still covered by the aforementioned protection range of "storing the energy storage circuit to the load".

Further optimizing the preferred embodiment, the air pump 3 operates intermittently. When the air pump 3 stops working, the power source 6 charges the energy storage circuit through the first stage boosting circuit. When the air pump 3 is in operation, the energy storage circuit is boosted by the second stage boosting circuit to supply power to the air pump 3.

In the preferred embodiment, the drive circuit further includes a switching circuit that controls its switching by a control signal CTRL. One end of the switch circuit is connected to the output end of the energy storage circuit, and the other end of the switch circuit is connected to the input end of the second stage boost circuit. Specifically, the switching circuit is turned on after the power of the energy storage circuit reaches a preset power, so that the second stage boosting circuit and the energy storage circuit are turned on, otherwise the switching circuit is disconnected, and the second stage boosting circuit is disconnected from the energy storage circuit. In another embodiment, the switching circuit is turned on after the voltage of the energy storage circuit reaches a preset voltage, so that the second stage boosting circuit and the energy storage circuit are turned on, otherwise the switching circuit is disconnected, so that the second stage boosting circuit and the energy storage circuit are disconnected. In still another embodiment, when the load is working, the control signal CTRL controls the switching circuit to be turned on, so that the second stage boosting circuit and the energy storage circuit are turned on, when the load stops working, the control signal CTRL controls the switch circuit to open, thereby disconnecting the second stage boost circuit from the energy storage circuit. The switching circuit controls the conduction and disconnection of the second stage boosting circuit and the energy storage circuit. When the load is working, the switching circuit controls the second stage boosting circuit to be turned on with the energy storage circuit, otherwise the second stage boosting circuit is disconnected from the energy storage circuit.

Figure 21:
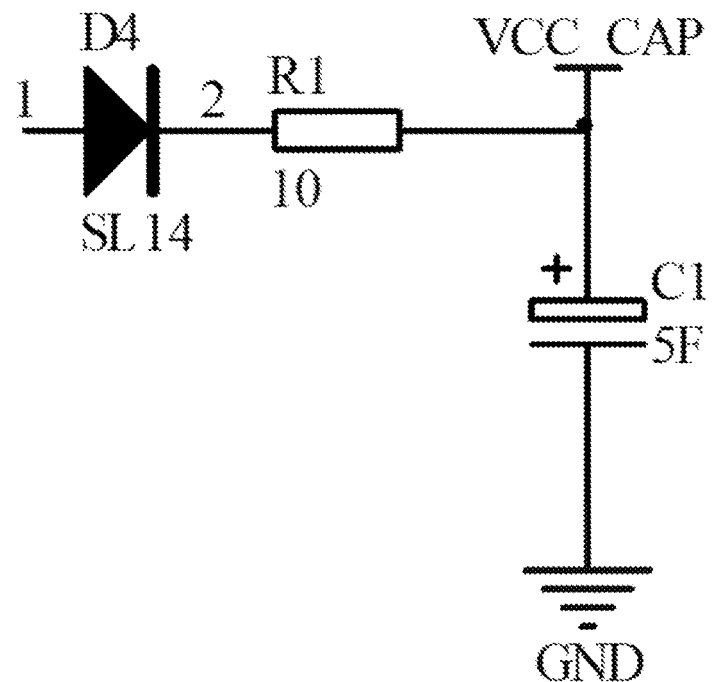
FIG. 21 is a circuit diagram of the energy storage circuit of FIG. 20.

Referring to FIG. 21, in the preferred embodiment, the energy storage circuit includes a super capacitor C1, a diode D4, and a resistor R1 (wherein the super capacitor C1 can also be replaced with a rechargeable battery). The anode of the diode D4 is connected to the output of the first stage booster circuit, and the cathode is connected to one end of the resistor R1. The other end of the resistor R1 is connected to the positive pole of the super capacitor C1, and the connection point is also connected to the input end of the second stage booster circuit and the voltage at the connection point is VCC_CAP. The negative pole of the super capacitor C1 is grounded. Among them, the voltage VCC_CAP is 1.8V-5.5V. The capacitance of the polar capacitor C1 is 2 F-50 F, the resistance of the resistor R1 is 100, and the diode D4 is a Schottky diode SL14. The energy storage circuit includes a super capacitor C1 or a rechargeable battery. That is, the first stage boosting circuit first boosts the power of the power source 6 to charge the rechargeable battery, and the rechargeable battery is boosted by the second stage boosting circuit to supply power to the load. The function of the energy storage circuit is mainly energy storage, that is, the energy storage circuit is a circuit that can charge and discharge. In the present embodiment, the super capacitor is selected for charging and discharging, and since the super capacitor can be charged and discharged hundreds of thousands of times, the power source 6 can be greatly protected. The resistor in the energy storage circuit is sized to limit the charging current, and the diode prevents current from flowing back. It is avoided that the current of the energy storage circuit is recirculated due to the absence of the power supply 6 for a long time, and the energy storage time required when the driving circuit is connected to the power supply 6 for the first time is reduced. A rechargeable battery such as a lithium battery can be used instead of the super capacitor C1, that is, the first stage boosting circuit first boosts the power of the power source to charge the rechargeable battery. The rechargeable battery is boosted by the second stage boost circuit to supply power to the load.

Figure 22:
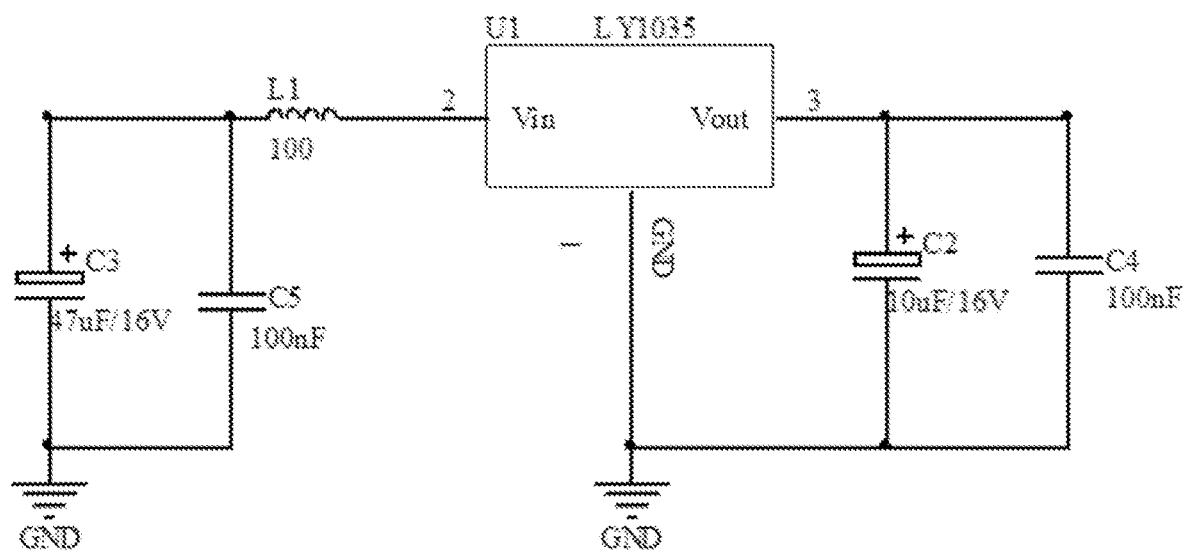
FIG. 22 is a circuit diagram of the first stage boosting circuit of FIG. 20.

Referring to FIG. 22, in the preferred embodiment, the first stage boosting circuit includes an inductor L1, a boosting chip one, a polar capacitor C2, C3, and a non-polar capacitor C4, C5. The anode of the capacitor C3 is connected to the anode of the power source 6, and the cathode is grounded. One end of the capacitor C5 is connected to the positive electrode of the capacitor C3, and the other end is grounded. One end of the inductor L1 is connected to the positive pole of the capacitor C3, and the input end of the boosting chip one is connected to the other end of the inductor L1. The grounding end of the boosting chip one is grounded, and the output end is connected to the positive pole of the capacitor C2. The negative pole of the capacitor C2 is grounded, the positive pole is also connected to one end of the capacitor C4, and the other end of the capacitor C4 is grounded. The output end of the boosting chip one, the positive pole of the capacitor C2, and one end of the capacitor C4 are connected to each other and the connection point is the output end of the first stage boosting circuit, and is connected to the anode of the diode D4. In this embodiment, the inductance of the inductor L1 is 100 H, the boost chip uses a boost chip LY1035, the polar capacitors C2 and C3 respectively use 47 uF/16V and 10 uF/16V capacitors, and the non-polar capacitors C4 and C5 use 100 nF capacitors.

The first stage boosting circuit boosts the voltage of the power source 6, and the output end is connected to the energy storage circuit to cause the power source 6 to charge the energy storage circuit through the first stage boosting circuit. At the same time, when the current of the power source 6 is unstable or the current is small, and the diode is provided, the unidirectionality of the diode can be used to charge the super capacitor, thereby stabilizing the flow and saving energy, and improving the energy utilization rate of the power source 6. The current of the first stage booster circuit is small, and even when the dry battery is running out of power (the current becomes smaller), the dry battery can still charge the super capacitor, which can greatly improve the utilization of the power of the power source 6. When the power source 6 is used with a battery, the power utilization rate of the battery can be increased to 80% or more, which can greatly improve the energy utilization rate of the battery.

Referring to FIG. 20, the switching circuit is controlled to be turned on and off by a control signal CTRL. One end of the switching circuit is connected to the output end of the energy storage circuit, and the other end of the switching circuit is connected to the input end of the second stage boosting circuit. The switching circuit controls the conduction and disconnection of the second stage boosting circuit and the energy storage circuit. Specifically, the switching circuit is turned on after the power of the energy storage circuit reaches a preset power, so that the second stage boosting circuit and the energy storage circuit are turned on. Otherwise, the switching circuit is turned off, causing the second stage boosting circuit to be disconnected from the energy storage circuit. In another embodiment, the switch circuit is turned on after the voltage of the energy storage circuit reaches a preset voltage, so that the second stage boost circuit and the energy storage circuit are turned on. Otherwise, the switching circuit is turned off, causing the second stage boosting circuit to be disconnected from the energy storage circuit. In still another embodiment, when the load is working, the control signal CTRL controls the switching circuit to be turned on, so that the second stage boosting circuit and the energy storage circuit are turned on. When the load stops working, the control signal CTRL controls the switch circuit to open, thereby disconnecting the second stage boost circuit from the energy storage circuit.

Figure 23:
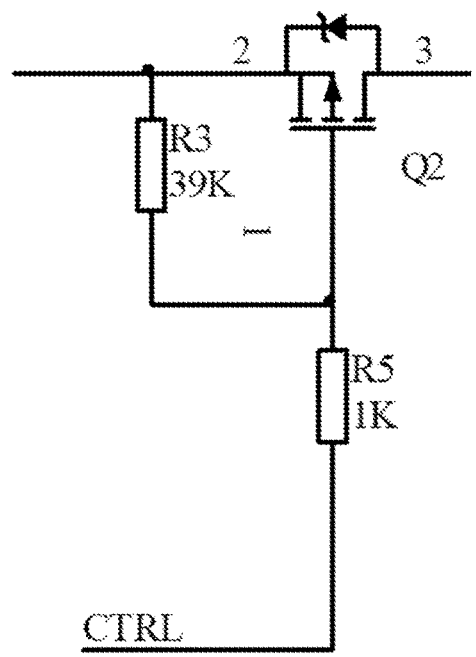
FIG. 23 is a circuit diagram of the switch circuit of FIG. 20.

Referring to FIG. 23, in the preferred embodiment, the switching circuit includes a P-channel MOS transistor Q2, a resistor R3, and a resistor R5. The source of the MOS transistor Q2 is connected to the anode of the super capacitor C1, and the drain of the MOS transistor Q2 is connected to the input terminal of the boost of the second stage. One end of the resistor R3 is connected to the source of the MOS transistor Q2, and the other end is connected to the gate of the MOS transistor Q2. One end of the resistor R5 is connected to the gate of the MOS transistor Q2, and the other end is connected to the control pin of the MCU of the single chip, that is, the control signal CTRL is accessed. The MCU control pin outputs a high level to turn off the switch circuit, and outputs a low level to open the switch circuit, thereby controlling the connection between the storage circuit and the second stage boost circuit. In the present embodiment, the resistance value of the resistor R3 is 39KΩ, and the resistance value of the resistor R5 is 1KΩ.

Figure 24:
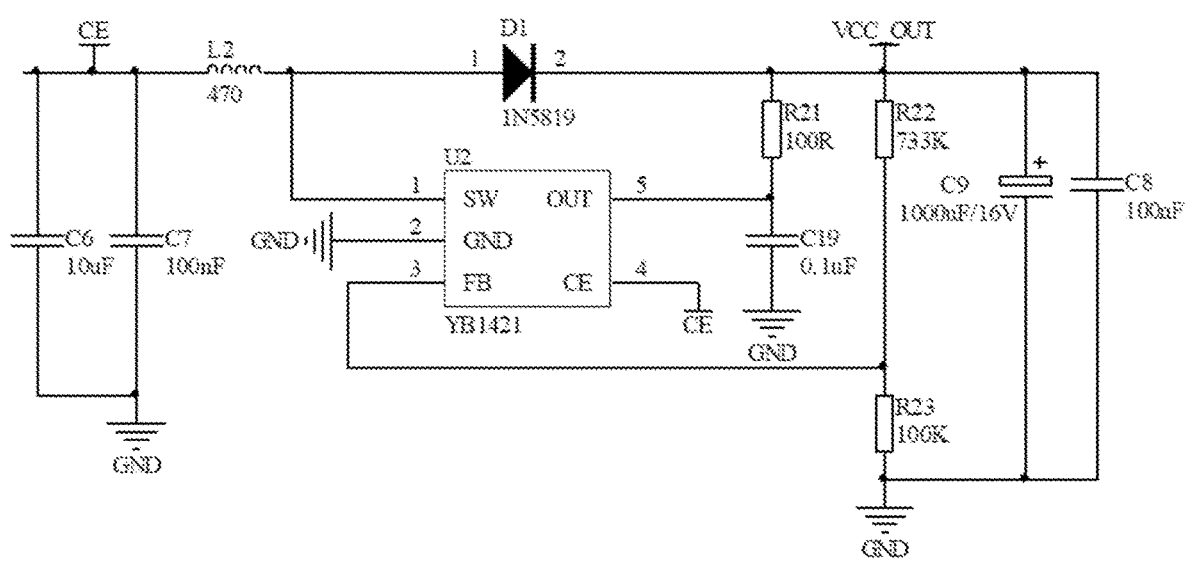
FIG. 24 is a circuit diagram of the second stage boosting circuit of FIG. 20.
Figure 25:
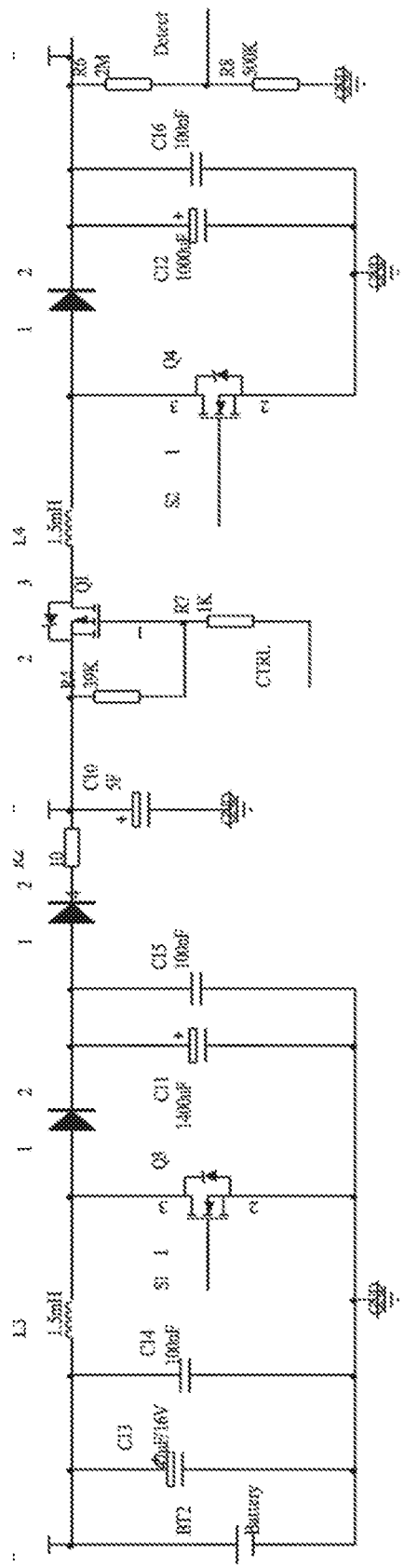
FIG. 25 is a drive circuit diagram of another preferred embodiment of the present invention.

Referring to FIG. 24, in the preferred embodiment, the second stage boosting circuit includes an inductor L2, a boosting chip 2, a diode D1, a non-polar capacitor C19, a resistor R21, a resistor R22, a resistor R23, a polar capacitor C9, and a non-polar capacitor C6, C7, and C8. One ends of the capacitors C6 and C7 are connected to the drain of the MOS transistor Q2, and the other ends are grounded. One end of the inductor L2 is connected to the drain of the MOS transistor Q2, and the conversion pin SW of the boosting chip 2 is connected to the other end of the inductor L2. The ground pin GND of the boost chip 2 is grounded, and the chip select terminal CE is connected to the drain of the MOS transistor Q2. The anode of the diode D1 is connected to the other end of the inductor L2. One end of the resistor R21 is connected to the negative electrode of the diode D1, and the other end is connected to the output pin OUT of the boosting chip 2. One end of the non-polarity capacitor C19 is connected to the other end of the resistor R21, and the other end is grounded, and one end of the resistor R22 is connected to one end of the resistor R21. One end of the resistor R23 is connected to the other end of the resistor R22, and the connection point is also connected to the feedback pin FB of the booster chip 2, and the other end is grounded. The positive pole of the capacitor C9 is connected to one end of the resistor R22, and the negative pole is grounded. One end of the capacitor C8 is connected to the positive electrode of the capacitor C9, and the other end is grounded.

Further optimization of the preferred embodiment, the negative electrode of diode D1, one end of resistor R21, one end of resistor R22, the anode of capacitor C9, one end of capacitor C8 are connected and the connection point is connected to the positive electrode of the load, and the negative pole of the load is grounded. Inductor L2 has an inductance of 470 H, booster chip 2 uses booster chip YB1421, diode D1 uses Schottky diode 1N5819, and resistors R21, R22, and R23 have resistance values of 100 R, 733 KΩ, and 100 KΩ, respectively. The capacitances of the non-polar capacitors C19, C6, C7, and C8 are 0.1 uF, 10 uF, 100 nF, and 100 nF, respectively, and the polar capacitor C9 uses a capacitor of 1000 uF/16V.

Further optimization of the preferred embodiment, when the switch circuit is turned on, the super capacitor supplies power to the load through the second stage boost circuit, and due to the characteristics of the super capacitor, the super capacitor can serve as a temporary current source for the second stage boost circuit and supply power to the load. The second-stage boosting circuit can supply sufficient voltage to the load when the charging circuit is completed (when the energy storage capacity reaches the preset power) and ensure the stability of the current discharged by the energy storage circuit. The second stage boost does not need to boost across a large voltage, making it easy to provide a short, large current to the load.

In the preferred embodiment, the initial voltage of the power source 6 is 1.1V-2.5V. As the power of the power source 6 is gradually consumed, the voltage of the power source 6 is gradually reduced, and the power can be supplied when the voltage is reduced to 0.9V, the first stage booster circuit boosts the voltage of the power supply 6 to about 2.6V-3.4V, and the second stage boost circuit boosts the voltage of the storage circuit to about 4.8V-6V. In other embodiments, the selection of the capacitor, the resistor, the inductor, the boosting chip, the diode, and the MOS transistor of the embodiment may be changed according to actual needs.

Referring to FIGS. 25-29, in another preferred embodiment, the scent diffusion device further includes a power source and a drive circuit, the drive circuit being coupled to the air pump, and the power source powering the air pump through the drive circuit. The power supply is a dry battery, and the power supply 6 can also select other portable power sources 6 such as a battery, and the load can be other intermittently working devices. The driving circuit includes a first stage boosting circuit for boosting the power supply, an energy storage circuit for receiving the output of the first stage boosting circuit, and a second stage boosting circuit for boosting the energy storage circuit; after the power supply is boosted by the first stage booster circuit, it is output to the energy storage circuit and charges the energy storage circuit; the second stage boost circuit boosts the voltage of the energy storage circuit to supply the load to the load. The driving circuit of this embodiment is similar to the above-described preferred embodiment, except that the device selection and the connection relationship of the first stage boosting circuit, the energy storage circuit, the switching circuit, and the second stage boosting circuit in the embodiment are different. The first stage boosting circuit and the second stage boosting circuit all use the Boost circuit, and the output of the second stage boosting circuit needs to use the MCU to detect the voltage, thereby ensuring that the output voltage is constant.

Further optimization of this other preferred embodiment, when the air pump stops working, the power supply charges the energy storage circuit through the first stage boosting circuit. When the air pump is working, the energy storage circuit is boosted by the second stage boosting circuit to supply power to the air pump.

In this other preferred embodiment, the driving circuit further includes a switching circuit that controls its switching by the control signal CTRL; one end of the switch circuit is connected to the output end of the energy storage circuit, and the other end of the switch circuit is connected to the input end of the second stage boost circuit; the switching circuit controls the conduction and disconnection of the second stage boosting circuit and the energy storage circuit. When the load is working, the switching circuit controls the second stage boosting circuit to be turned on with the energy storage circuit, otherwise the second stage boosting circuit is disconnected from the energy storage circuit.

Figure 26:
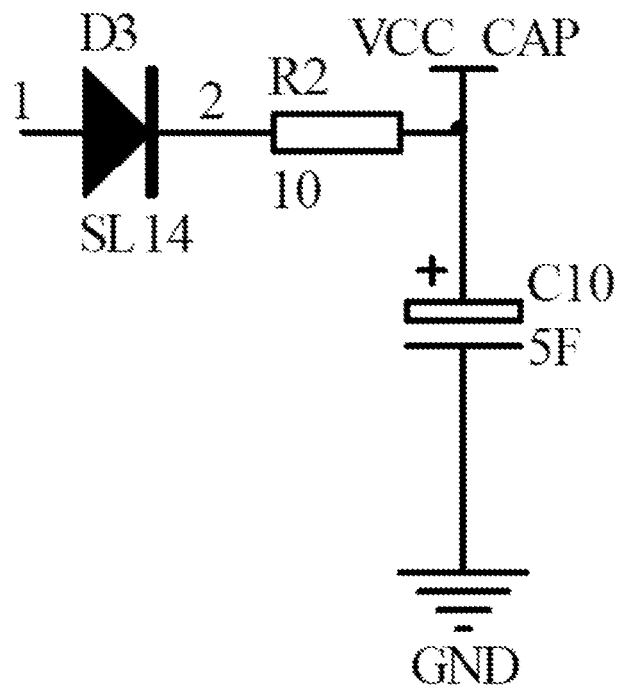
FIG. 26 is a circuit diagram of the energy storage circuit of FIG. 25.

Referring to FIG. 26, in this further preferred embodiment, the energy storage circuit includes a supercapacitor C1 or a rechargeable battery. The energy storage circuit includes a super capacitor C10, a diode D3, and a resistor R2. The anode of the diode is connected to the output end of the first stage booster circuit, the negative pole is connected to the battery; the other end of the resistor is connected to the positive pole of the super capacitor and the connection point is also connected to one end of the switch circuit; the other end of the super capacitor is grounded. In this embodiment, the capacitance of the super capacitor C10 is 2 F-50 F, the diode D3 is a Schottky diode SL14, and the resistance of the resistor R2 is 100.

Figure 27:
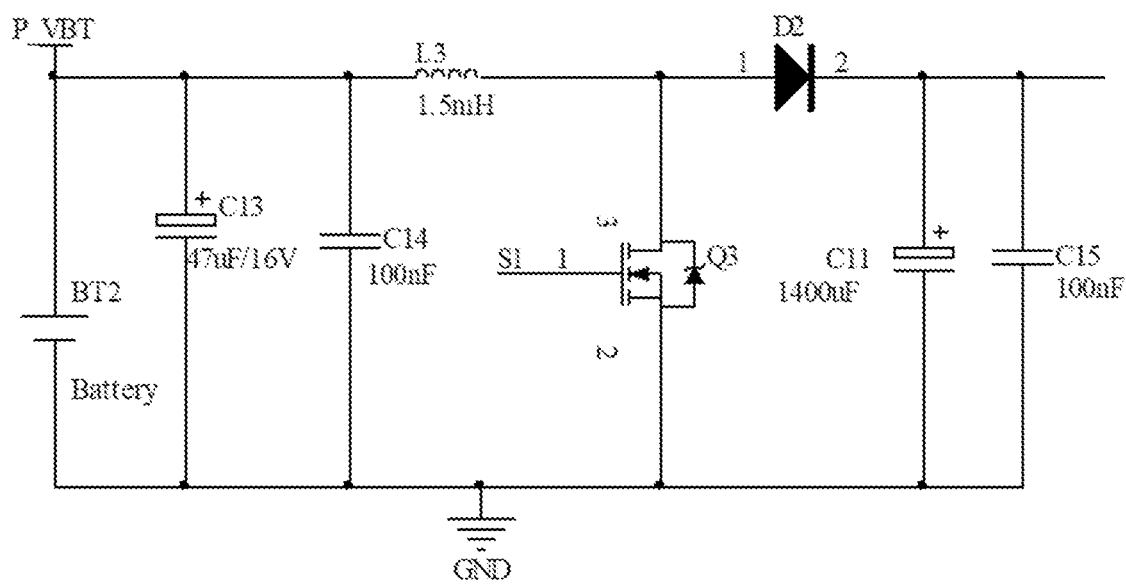
FIG. 27 is a circuit diagram of the first stage boosting circuit of FIG. 25.

Referring to FIG. 27, in the other preferred embodiment, the first stage boosting circuit includes an inductor L3, a MOS transistor Q3, a polar capacitor C13, C11, a non-polar capacitor C14, C15, and a diode D2. The positive electrode having the polar capacitor C13 is connected to the positive electrode of the power source BT2, and the negative electrode is grounded. One end of the non-polarity capacitor C14 is connected to the positive pole of the power source BT2, and the other end is grounded. One end of the inductor L3 is connected to the positive electrode of the power source BT2. The source of the MOS transistor Q3 is grounded, the drain is connected to the other end of the inductor L3, and the gate is connected to a signal S1. The anode of the diode D2 is connected to the source of the MOS transistor Q3. The positive electrode having the polar capacitor C11 is connected to the negative electrode of the diode D2, and the negative electrode of the capacitor C11 is grounded. One end of the non-polarity capacitor C15 is connected to the cathode of the diode, and the other end is grounded. In the present embodiment, the inductance of the inductor L3 is 1.5 mH, and the MOS transistor Q3 is the transistor AO3400. Capacitors C13 and C11 use 47 uF/16V and 1400 uF/16V capacitors respectively, and capacitors C14 and C15 use 100 nF capacitors. Diode D2 uses a Schottky diode 1N5819.

For further optimization of the preferred embodiment, the MCU controls the switching of the MOS transistor Q3 by outputting a signal S1 (PWM signal) to implement boosting of the boost circuit.

Figure 28:
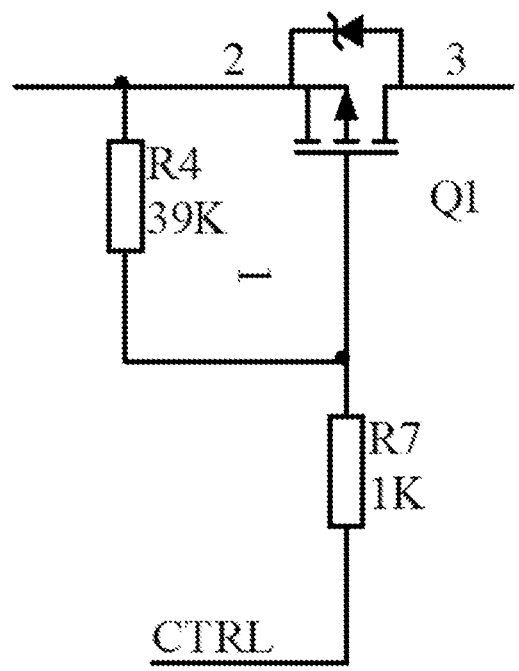
FIG. 28 is a circuit diagram of the switch circuit of FIG. 25.

Referring to FIG. 28, in this other preferred embodiment, the switching circuit includes a P-channel MOS transistor Q1, a resistor R4, and a resistor R7. The source of the MOS transistor Q1 is connected to the anode of the super capacitor C10, and the drain is connected to the input terminal of the boost of the second stage. One end of the resistor R4 is connected to the source of the MOS transistor Q1, and the other end is connected to the gate of the MOS transistor Q1. One end of the resistor R7 is connected to the gate of the MOS transistor Q1, and the other end is connected to the control pin of the MCU of the single chip, that is, the control signal CTRL is accessed. The control pin of the MCU of the single chip outputs a high level to turn off the switch circuit, and outputs a low level to open the switch circuit, thereby controlling the connection between the energy storage circuit and the second stage boost circuit. In the present embodiment, the resistance values of the resistor R4 and the resistor R7 are respectively 39 KΩ and 1 KΩ.

Figure 29:
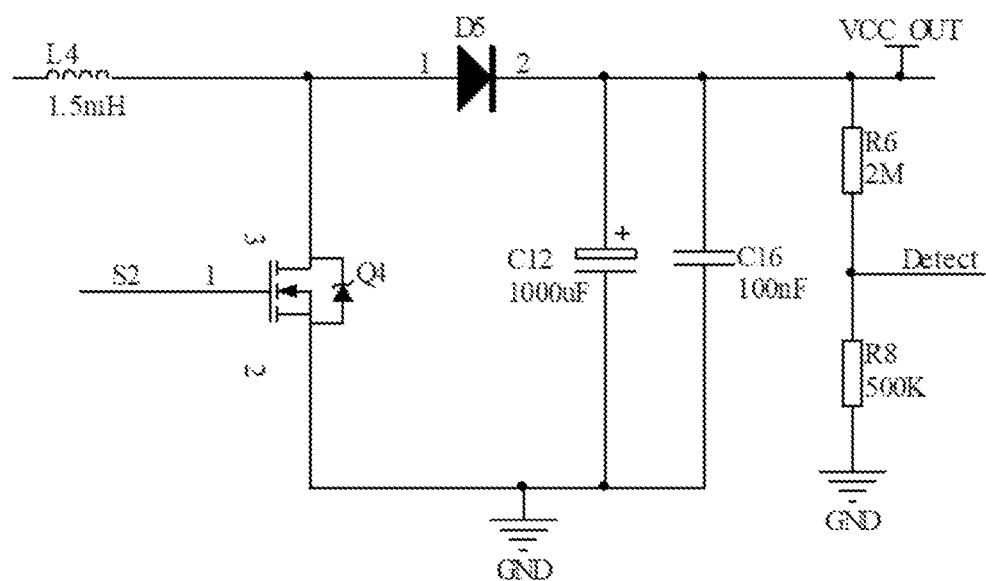
FIG. 29 is a circuit diagram of the second stage boosting circuit of FIG. 25.

Referring to FIG. 29, in the other preferred embodiment, the second stage boosting circuit includes an inductor L4, a MOS transistor Q4, a diode D5, a gradation capacitor C12, a non-polarity capacitor C16, a resistor R6, and a resistor R8. One end of the inductor L4 is connected to the drain of the MOS transistor Q1. The source of the MOS transistor Q4 is grounded, the drain is connected to the other end of the inductor L4, and the gate is connected to a signal S2. The anode of the diode D5 is connected to the drain of the MOS transistor Q4. The positive electrode having the polar capacitor C12 is connected to the negative electrode of the diode D5, and the negative electrode thereof is grounded. The non-polarity capacitor C16 has one end connected to the cathode of the diode D5 and the other end grounded. One end of the resistor R6 is connected to the cathode of the diode D5, and the other end outputs an output signal Detect. One end of the resistor R8 is connected to the resistor R6, and the other end is grounded. In the present embodiment, the inductance of the inductor L4 is 1.5 mH, and the MOS transistor Q4 is the transistor AO3400. Diode D5 uses Schottky diode 1N5819, capacitor C12 uses 1000 uF/16V capacitor, and capacitor C16 uses 100 nF capacitor. The resistance values of the resistors R6 and R8 are 2 MΩ and 500 KΩ, respectively.

For further optimization of the other preferred embodiment, the MCU controls the switching of the Boost circuit by outputting a signal S2 (PWM signal) to the MOS transistor Q4 to control its switching. The resistors R8 and R6 divide voltage to provide a voltage signal to the MCU of the single-chip microcomputer, so that the MCU of the single-chip microcomputer adjusts the frequency of the PWM signal according to the voltage signal to realize a constant voltage output.

In the circuit of the other preferred embodiment, by providing a plurality of diodes to prevent the MOS transistor from being damaged by the reverse voltage, the microcontroller MCU outputs two PWM signals (signals S1, S2). The two Boost circuits are boosted, and the control circuit CTRL is used to control the discharge of the second circuit by the energy storage circuit, and the PWM frequency of the signal S2 is detected by the voltage of the detection signal Detect to realize a constant voltage output. When the load does not need to work, the signal S2 outputs a low voltage, and the control signal CTRL outputs a high level to reduce the loss. Since the boosting amplitude of each stage is small, the operating current of the power supply is also small, the power supply is reduced, and the energy utilization rate of the power source is improved. At the same time, the super capacitor supplies power to the load through the second stage boosting circuit, and when the power supply current is unstable, it can stabilize the flow and ensure the stability of the load current. And the super capacitor can be charged and discharged hundreds of thousands of times, which is beneficial to protect the power supply. After the power supply is used for a period of time, even if the operating current of the power supply becomes smaller, the super capacitor can still be charged, and the power can be greatly utilized. When the power supply uses a dry battery, the utilization rate of the battery can be increased to more than 80%, which can greatly improve the energy utilization rate of the dry battery.

The other preferred embodiment is different from the above preferred embodiment in that the embodiment does not need to use a boosting chip, can simplify the circuit, improve the stability of the circuit, and can improve the service life of the driving circuit.

The driving circuit of the scent diffusion device can realize intermittent operation of the air pump. When the air pump stops working, the atomizing device stops atomizing, and at this time, the power source charges the energy storage circuit through the first stage boosting circuit. When the air pump is working, the atomizing device starts to atomize, and the energy storage circuit is boosted by the second stage boosting circuit to supply power to the air pump.

In summary, the driving circuit of the scent diffusion device has the following advantages compared with the prior art:

(1) The driving circuit of the scent diffusion device is boosted by setting a first stage boosting circuit and a second stage boosting circuit, and a super capacitor is disposed between the first stage boosting circuit and the second stage boosting circuit, so that the power source charges the super capacitor through the first stage boosting circuit. Moreover, due to the small boosting range, the operating current of the power supply is also small, reducing the heat generation of the power supply and improving the energy utilization rate of the power supply.

(2) At the same time, the driving circuit of the scent diffusion device disconnects the energy storage circuit and the second stage boosting circuit by setting a switching circuit, so that the super capacitor can better store energy. The resistance in the energy storage circuit is adjustable to limit the charging current, the diode prevents the current from flowing back, avoiding the current backflow of the energy storage circuit due to the long absence of the power supply, and reducing the energy storage time required for the first time the drive circuit is connected to the power supply. After the second stage upgrade circuit is turned on, the super capacitor supplies power to the load through the second stage boost circuit, when the power supply current is unstable, it can play a role of steady current, ensure the stability of the load current, and the super capacitor can be charged and discharged hundreds of thousands of times, which is beneficial to protect the power supply.

The current of the first stage booster circuit is small, and even when the dry battery is running out of power (the current becomes smaller), the dry battery can still charge the super capacitor, which can greatly improve the utilization of the power of the power source. When the power source uses a battery, the power utilization rate of the battery can be increased to 80% or more, which can greatly improve the energy utilization rate of the battery.

The second stage boosting circuit can supply sufficient voltage to the load when the charging circuit is completed (when the energy storage capacity reaches the preset power) and ensure the stability of the current discharged by the energy storage circuit. The second stage boost does not need to boost across a large voltage, making it easy to provide a short, large current to the load.

Therefore, the above drive circuit is very suitable for the intermittent work of the scent diffusion device and can also be used in other similar products to improve the energy utilization rate of the product and improve the stability of the product work.

The other end of the liquid passage of the atomizing core of the embodiment of the present invention shrinks to form a liquid outlet, so the liquid passage does not need to be too thin, as long as the liquid outlet is small enough to save the essential oil and spray a sufficiently fine spray. The gas passage uses the same principle as the liquid passage, which reduces the difficulty of processing. In addition, the widened liquid passage can also reduce the possibility of blockage.

The above is only a preferred embodiment of the present invention, and thus does not limit the scope of the patent of the present invention. The equivalent structure or equivalent process transformation made by using the specification and the drawings of the present invention, or directly or indirectly applied to other related technical fields, are all included in the scope of patent protection of the present invention.

What is claimed is:

1. A scent diffusion device, comprising: an air pump, an atomizer and a liquid storage bottle, wherein the atomizer is connected to the air pump and the liquid storage bottle, an atomizing chamber is disposed in the atomizer, a gas passage and a liquid passage is disposed in the atomizer, one end of the gas passage is connected to the air pump through a vent line, and the other end is contracted to form a gas outlet, one end of the liquid passage is connected to an inside of the liquid storage bottle through a pipe, and the other end is contracted to form a liquid outlet, the atomizing chamber is connected to the gas outlet and the liquid outlet, and the atomizer is further provided with a mist outlet connected to the atomizing chamber;
wherein the atomizer comprises an atomizing base and an atomizing core, the atomizing base is connected to the air pump, the atomizing core is mounted on the atomizing base, and the gas outlet and the liquid outlet are both disposed on the atomizing core;
wherein the atomizing base is provided with a convex air guiding tube and a convex liquid suction tube, the air guiding tube and the liquid suction tube are arranged in parallel and spaced apart, the atomizing core is arranged with an air guiding hole and a liquid guiding hole which are parallelly spaced, the air guiding tube and the liquid suction tube are respectively inserted into the air guiding hole and the liquid guiding hole, the air guiding tube is connected to the air pump, and the liquid suction tube is connected to the pipe.

2. The scent diffusion device according to claim 1, wherein a ratio of a maximum inner diameter of one end of the gas passage connected to the vent line to an inner diameter of the gas outlet is between 5 and 20, and/or
a ratio of a maximum inner diameter of one end of the liquid passage connected to the pipe to an inner diameter of the liquid outlet is between 5 and 20.

3. The scent diffusion device according to claim 1, wherein a bottom wall of at least a portion of the vent line is higher than the gas outlet; and/or
the mist outlet is inclined from the inside to an outside with respect to the liquid storage bottle.

4. The scent diffusion device according to claim 1, wherein the scent diffusion device further comprises an outer housing and an inner housing, the inner housing being mounted in the outer housing and detachably connected to an inner wall of the outer housing, an air pump installation chamber is formed on the inner housing, the air pump is installed in the air pump installation chamber, the inner housing is further provided with an air pump connection joint, and the air pump connection joint is connected to the air pump through a gas pipe; the atomizer and the liquid storage bottle are installed in the outer housing and outside the inner housing, the atomizer is provided with an atomizing connection joint, the atomizing connection joint is connected to the gas passage, and the atomizing connection joint is plugging sealed with the air pump connection joint.

5. The scent diffusion device according to claim 4, wherein a plurality of buckles is disposed on the inner wall of the outer housing, the inner housing is provided with a plurality of holders engaged with the buckles respectively, and the inner housing is detachably coupled to the inner wall of the outer housing by the buckles and the holders.

6. The scent diffusion device according to claim 5, wherein a limiting member is further fixed on the inner wall of the outer housing, the limiting member is an elastic member, and the limiting member abuts on an outer wall of the inner housing.

7. The scent diffusion device according to claim 1, further comprising an outer housing and an inner housing, the inner housing being mounted in the outer housing, wherein the inner housing is formed with an air pump installation chamber, the air pump is installed in the air pump installation chamber, an air pump connection joint is further disposed on the inner housing, the air pump connection joint is connected to the air pump through a gas pipe, the atomizer and the liquid storage bottle are installed in the outer housing and outside the inner housing, and the atomizer is provided with an atomizing connection joint, the atomizing connection joint is connected to the gas passage, the air pump connection joint is made of a silicone material, and the atomizing connection joint is inserted into the air pump connection joint to be in sealing engagement with the air pump connection joint.

8. The scent diffusion device according to claim 1, wherein the atomizer further comprises an atomizing cover, the atomizing base is connected to the atomizing cover, the atomizing chamber is formed in the atomizing cover or between the atomizing cover and the atomizing base, the atomizing cover is formed with the mist outlet, and the atomizing core is located in the atomizing chamber.

9. The scent diffusion device according to claim 8, wherein an atomizing connection joint is formed on the atomizing cover, and the atomizing connection joint is connected to the air pump, a connecting post is formed on the atomizing base, the connecting post is detachably inserted into the atomizing cover to fix the atomizing base in the atomizing cover, the connecting post is connected to the atomizing connection joint and the air guiding tube, a lower end of the atomizing cover is provided with a liquid storage bottle connector, and the liquid storage bottle is detachably connected with the liquid storage bottle connector.

10. A scent diffusion device, comprising: an air pump, an atomizer and a liquid storage bottle, wherein the atomizer is connected to the air pump and the liquid storage bottle, the atomizer is provided with a gas outlet and a liquid outlet;
wherein the atomizer comprises an atomizing base, an atomizing core and an atomizing cover, the atomizing core is mounted on the atomizing base, the atomizing base is connected to the atomizing cover;
wherein the atomizing base is provided with an air guiding tube, a liquid suction tube, a connecting post and a pipe connection joint; the air guiding tube, the liquid suction tube and the connecting post are arranged on one end of the atomizing base, and the pipe connection joint is disposed on an opposite end of the atomizing base, the air guiding tube and the liquid suction tube are arranged side by side and on a same side of the connecting post; the liquid suction tube is connected to the pipe connection joint, the pipe connection joint is connected to an inside of the liquid storage bottle through a pipe; and the connecting post is detachably inserted into the atomizing cover to fix the atomizing base in the atomizing cover;

wherein the gas outlet and the liquid outlet are both disposed on the atomizing core; the atomizing core is further provided with an air guiding hole and a liquid guiding hole, the gas outlet and the liquid outlet are respectively connected to the air guiding hole and the liquid guiding hole, and the air guiding tube and the liquid suction tube are respectively inserted into the air guiding hole and the liquid guiding hole; and wherein the atomizing cover is formed with an outwardly convex atomizing connection joint, the outwardly convex atomizing connection joint is connected to the air pump; and the atomizing connection joint is connected to the air guiding tube through the connecting post.

11. The scent diffusion device according to claim 10, wherein the air guiding tube and the liquid suction tube both are oblique with respect to the connecting post, and the air guiding tube and the liquid suction tube both are oblique with respect to the pipe connection joint.

* * * * *